US008024128B2

(12) United States Patent
Rabinowitz et al.

(10) Patent No.: US 8,024,128 B2
(45) Date of Patent: Sep. 20, 2011

(54) SYSTEM AND METHOD FOR IMPROVING CLINICAL DECISIONS BY AGGREGATING, VALIDATING AND ANALYSING GENETIC AND PHENOTYPIC DATA

(75) Inventors: Matthew Rabinowitz, Portola Valley, CA (US); Wayne Chambliss, New York, NY (US); John Croswell, Seattle, WA (US); Miro Sarbaev, Palo Alto, CA (US); Milena Banjevic, New York, NY (US)

(73) Assignee: Gene Security Network, Inc., Redwood City, CA (US)

( * ) Notice: Subject to any disclaimer, the term of this patent is extended or adjusted under 35 U.S.C. 154(b) by 1012 days.

(21) Appl. No.: 11/004,274

(22) Filed: Dec. 3, 2004

(65) Prior Publication Data
US 2006/0052945 A1 Mar. 9, 2006

Related U.S. Application Data

(60) Provisional application No. 60/607,506, filed on Sep. 7, 2004.

(51) Int. Cl.
*G01N 33/50* (2006.01)
(52) U.S. Cl. .............................. 702/19; 600/300; 703/2
(58) Field of Classification Search .................. None
See application file for complete search history.

(56) References Cited

U.S. PATENT DOCUMENTS

| 5,635,366 | A | | 6/1997 | Cook |
|---|---|---|---|---|
| 5,824,467 | A | | 10/1998 | Mascarenhas |
| 5,860,917 | A | * | 1/1999 | Comanor et al. ............ 600/300 |
| 5,994,148 | A | | 11/1999 | Stewart |
| 6,025,128 | A | | 2/2000 | Veltri |
| 6,108,635 | A | * | 8/2000 | Herren et al. ..................... 705/2 |
| 6,180,349 | B1 | | 1/2001 | Ginzinger et al. |
| 6,258,540 | B1 | | 7/2001 | Lo et al. |
| 6,489,135 | B1 | | 12/2002 | Parrott |
| 6,720,140 | B1 | | 4/2004 | Hartley |
| 6,958,211 | B2 | | 10/2005 | Vingerhoets |
| 7,035,739 | B2 | | 4/2006 | Schadt |
| 7,058,517 | B1 | | 6/2006 | Denton |
| 7,058,616 | B1 | | 6/2006 | Larder |
| 7,218,764 | B2 | | 5/2007 | Vaisberg |
| 7,297,485 | B2 | | 11/2007 | Bornarth |
| 7,332,277 | B2 | | 2/2008 | Dhallan |
| 7,442,506 | B2 | | 10/2008 | Dhallan |
| 7,645,576 | B2 | | 1/2010 | Lo et al. |
| 7,700,325 | B2 | | 4/2010 | Cantor et al. |
| 7,718,370 | B2 | | 5/2010 | Dhallan |
| 7,838,647 | B2 | | 11/2010 | Hahn et al. |
| 7,888,017 | B2 | | 2/2011 | Quake et al. |
| 2003/0009295 | A1 | * | 1/2003 | Markowitz et al. ............ 702/20 |
| 2003/0065535 | A1 | * | 4/2003 | Karlov et al. ..................... 705/2 |
| 2003/0101000 | A1 | | 5/2003 | Bader et al. |
| 2003/0228613 | A1 | | 12/2003 | Bornarth |
| 2004/0033596 | A1 | | 2/2004 | Threadgill |
| 2004/0137470 | A1 | | 7/2004 | Dhallan |
| 2004/0236518 | A1 | | 11/2004 | Pavlovic |
| 2004/0259100 | A1 | | 12/2004 | Gunderson |
| 2005/0009069 | A1 | | 1/2005 | Liu et al. |
| 2005/0049793 | A1 | | 3/2005 | Paterlini-Brechot et al. |
| 2005/0144664 | A1 | * | 6/2005 | Smith et al. ................... 800/266 |
| 2005/0250111 | A1 | | 11/2005 | Xie |
| 2005/0272073 | A1 | | 12/2005 | Vaisberg |
| 2006/0040300 | A1 | | 2/2006 | Dapprich |
| 2006/0057618 | A1 | | 3/2006 | Piper et al. |
| 2006/0121452 | A1 | | 6/2006 | Dhallan |
| 2006/0134662 | A1 | | 6/2006 | Pratt |
| 2006/0141499 | A1 | | 6/2006 | Sher |
| 2006/0229823 | A1 | | 10/2006 | Liu et al. |
| 2007/0027636 | A1 | | 2/2007 | Rabinowitz |
| 2007/0059707 | A1 | | 3/2007 | Cantor |
| 2007/0122805 | A1 | | 5/2007 | Cantor et al. |
| 2007/0178478 | A1 | | 8/2007 | Dhallan et al. |
| 2007/0178501 | A1 | | 8/2007 | Rabinowitz |
| 2007/0184467 | A1 | | 8/2007 | Rabinowitz |
| 2007/0207466 | A1 | | 9/2007 | Cantor et al. |
| 2007/0212689 | A1 | | 9/2007 | Bianchi et al. |

(Continued)

FOREIGN PATENT DOCUMENTS

WO    WO 03/031646    4/2003

(Continued)

OTHER PUBLICATIONS

Allaire et al. (Theor. Appl. Genet., vol. 57, p. 267-272, 1980).*
Page et al. (Science, vol. 301, p. 785-789, Aug. 8, 2003).*
Beerenwinkel et al. (Nucleic Acids Research, vol. 31, No. 13, p. 3850-3855, 2003).*
Streyerberg et al. (Statistica Neerlandica, vol. 55, No. 1, p. 76-88, 2001).*
Singer (Proceedings. IEEE International Symposium on Information Theory, p. 286, Jul. 4, 2003).*
McCray et al. (Medinfo2001, vol. 84, Ed. V. Patel et al., IOS press, p. 216-220, 2001).*

(Continued)

*Primary Examiner* — Karlheinz R Skowronek
(74) *Attorney, Agent, or Firm* — Greenberg Traurig, LLP; David J. Dykeman; Danielle T. Abramson

(57) ABSTRACT

The information management system disclosed enables caregivers to make better decisions by using aggregated data. The system enables the integration, validation and analysis of genetic, phenotypic and clinical data from multiple subjects. A standardized data model stores a range of patient data in standardized data classes comprising patient profile, genetic, symptomatic, treatment and diagnostic information. Data is converted into standardized data classes using a data parser specifically tailored to the source system. Relationships exist between standardized data classes, based on expert rules and statistical models, and are used to validate new data and predict phenotypic outcomes. The prediction may comprise a clinical outcome in response to a proposed intervention. The statistical models and methods for training those models may be input according to a standardized template. Methods are described for selecting, creating and training the statistical models to operate on genetic, phenotypic, clinical and undetermined data sets.

17 Claims, 12 Drawing Sheets

U.S. PATENT DOCUMENTS

| | | |
|---|---|---|
| 2007/0259351 A1 | 11/2007 | Chinitz et al. |
| 2008/0020390 A1 | 1/2008 | Mitchell et al. |
| 2008/0070792 A1 | 3/2008 | Stoughton et al. |
| 2008/0102455 A1 | 5/2008 | Poetter |
| 2008/0138809 A1 | 6/2008 | Kapur |
| 2008/0182244 A1 | 7/2008 | Tafas |
| 2008/0243398 A1 | 10/2008 | Rabinowitz |
| 2009/0029377 A1 | 1/2009 | Lo et al. |
| 2010/0138165 A1 | 6/2010 | Fan et al. |
| 2010/0171954 A1 | 7/2010 | Quake et al. |
| 2010/0256013 A1 | 10/2010 | Quake et al. |
| 2011/0033862 A1 | 2/2011 | Rabinowitz et al. |
| 2011/0092763 A1 | 4/2011 | Rabinowitz et al. |

FOREIGN PATENT DOCUMENTS

| | | |
|---|---|---|
| WO | WO 2007/057647 | 5/2007 |
| WO | WO 2007/062164 | 5/2007 |
| WO | WO 2007/070482 | 6/2007 |
| WO | WO 2008/115497 | 9/2008 |
| WO | WO 2009/013492 | 1/2009 |
| WO | WO 2009/013496 | 1/2009 |
| WO | WO 2009/019455 | 2/2009 |
| WO | WO 2009/105531 | 8/2009 |
| WO | WO 2009/146335 | 12/2009 |
| WO | WO 2010/017214 | 2/2010 |
| WO | WO 2011/041485 | 4/2011 |

OTHER PUBLICATIONS

Coyle et al. (International Journal of Medical Informatics 69 (2003) 157174).*
Abidi et al. (International Journal of Medical Informatics, vol. 68, p. 187-203, 2002).*
Fixed medium. (1992). In Academic Press Dictionary of Science and Technology. Retrieved from www.credoreference.com/entry/apdst/fixed_medium, accessed on Nov. 18, 2009.*
Hojsgaard et al. (Computational Statistics and Data Analysis, vol. 19, p. 155-175, 1995).*
Random variable. (2008). In the Penguin Dictionary of Mathematics. Retrieved from http://www.credoreference.com/entry/penguinmath/random_variable.*
Bada & Altman, Computational Modeling of Structural Experimental Data, In Methods in Enzymology, RNA—Ligand Interactions, Part A, vol. 317, 470-491 (2000).
Bodenreider, The Unified Medical Language System (UMLS): Integrating Biomedical Terminology, Nucleic Acids Research, 32:D267-D270 (2004).
Rabinowitz, et al., Accurate Prediction of HIV-1 Drug Response from the Reverse Transcriptase and Protease Amino Acid Sequences Using Sparse Models Created by Convex Optimization, Bioinformatics, 22(5):541-549 (2006).
Stevens, et al., Ontology-Based Knowledge Representation for Bioinformatics, Briefings in Bioinformatics, 1 (4):398-414 (2000).
Troyanskaya, et al., A Bayesian Framework for Combining Heterogeneous Data Sources for Gene Function Prediction (in *Saccharomyces cerevisiae*), Proc. Nat. Academy of Sci., 100(14):8348-8353 (2003).
Yeh, et al., Knowledge Acquisition, Consistency Checking and Concurrency Control for Gene Ontology (GO), Bioinformatics, 19(2):241-248 (2003).
Beaumont et al., The Bayesian Revolution in Genetics, Nature Reviews Genetics, 5 (4), p. 251-261 (Apr. 2004).
Beerenwinkel et al., Methods for Optimizing Antiviral Combination Therapies, Bioinformatics, 19 (3), p. i16-i25 (Jul. 2003).
Breithaupt, The Future of Medicine, European Molecular Biology Organization, 2 (6), p. 465-467 (Jun. 2001).
Colella et al., QuantiSNP: an Objectives Bayes Hidden-Markov Model to Detect and Accurately Map Copy Number Variation Using SNP Genotyping Data, Nucleic Acids Research, 35 (6), p. 2013-2025 (Mar. 2007).
Donoso et al., Current Value of Preimplantation Genetic Aneuploidy Screening in IVF, Hum. Reprod. Update, 13 (1), p. 15-25 (Jan./Feb. 2007).
Fiorentino et al., Development and Clinical Application of a Strategy for Preimplantation Genetic Diagnosis of Single Gene Disorders Combined with HLA Matching, Molecular Human Reproduction, 10 (6), p. 445-460 (Jun. 2004).
Fiorentino et al., Short Tandem Repeats Haplotyping of the HLA Region in Preimplantation HLA Matching, European J. Human Genetics, 13 (8), p. 953-958 (Aug. 2005).
Fiorentino et al., Strategies and Clinical Outcome of 250 Cycles of Preimplantation Genetic Diagnosis for Single Gene Disorders, Human Reproduction, 21 (3), p. 670-684 (Mar. 2006).
Freeman et al., Copy Number Variation: New Insights in Genome Diversity, Genome Research, 16 (8), p. 949-961 (Aug. 2006).
Harper et al., Recent Advances and Future Developments in PGD, Prenatal Diagnosis, 19, p. 1193-1199 (Dec. 1999).
Hellani et al., Clinical Application of Multiple Displacement Amplification in Preimplantation Genetic Diagnosis, Reproductive BioMedicine Online, 10 (3), p. 376-380 (Jan. 13, 2005).
Hollox et al., Extensive Normal Copy Number Variation of a β-Defensin Antimicrobial-Gene Cluster, Am. J. Hum. Genet., 73 (3), p. 591-600 (Sep. 2003).
Hu et al., Aneuploidy Detection in Single Cells Using DNA Array-Based Comparative Genomic Hybridiation, Molecular Human Reproduction, 10 (4), p. 283-289 (Apr. 2004).
Kijak et al., Discrepant Results in the Interpretation of HIV-1 Drug-Resistance Genotypic Data Among Widely Used Algorithms, HIV Medicine, 4 (1), p. 72-78 (Jan. 2003).
Kuliev et al., Thirteen Years' Experience on Preimplantation Diagnosis: Report of the Fifth International Symposium on Preimplantation Genetics, Reproductive BioMedicine Online, 8 (2), p. 229-235 (Dec. 22, 2003).
Munne et al., Chromosome Abnormalities in Human Embryos, Textbook of Assisted Reproductive Techniques, p. 355-377 (Jul. 2004).
Ogino et al., Bayesian Analysis and Risk Assessment in Genetic Counseling and Testing, Journal of Molecular Diagnostics, (6) 1, p. 1-9 (Feb. 2004).
Rechitsky et al., Preimplantation Genetic Diagnosis with HLA Matching, Reproductive BioMedicine Online, 9 (2), p. 210-221 (Jun. 23, 2004).
Renwick et al., Proof of Principle and First Cases Using Preimplantation Genetic Haplotyping—A Paradigm Shift for Embryo Diagnosis, Reproductive BioMedicine Online, 13 (1), p. 110-119 (Apr. 28, 2006).
Sander, Genetic Medicine and the Future of Health Care, Science, 287 (5460), p. 1977-1978 (Mar. 17, 2000).
Sweetkind-Singer, Log-Penalized Linear Regression, International Symposium on Information Theory, p. 286 (Jun. 29-Jul. 4, 2003).
Slater et al., High-Resolution Identification of Chromosomal Abnormalities Using Oligonucleotide Arrays Containing 116,204 SNPs, Am. J. Human Genetics, 77 (5), p. 709-726 (Nov. 2005).
Stephens, et al., A Comparison of Bayesian Methods for Haplotype Reconstruction from Population Genotype Data, Am. J. Human Genetics, 73 (5), p. 1162-1169 (Nov. 1, 2003).
Strom et al., Neonatal Outcome of Preimplantation Genetic Diagnosis by Polar Body Removal: the first 109 infants, Pediatrics, (4), p. 650-653 (Oct. 2000).
Verlinsky et al., Over a Decade of Experience with Preimplantation Genetic Diagnosis, Fertility and Sterility, 82 (2), p. 302-303 (Aug. 2004).
Wells, Advances in Preimplantation Genetic Diagnosis, European J. of Obstetrics and Gynecology and Reproductive Biology, 115S, p. S97-S101 (Jul. 1, 2004).
Wells, Microarray for Analysis and Diagnosis of Human Embryos, 12th International Congress on Prenatal Diagnosis and Therapy, p. 9-17 (Jun. 24-27, 2004).
Wilton, Preimplantation Genetic Diagnosis and Chromosome Analysis of Blastomeres Using Comparative Genomic Hybridization, Hum. Record. Update, (11) 1, p. 33-41 (Jan./Feb. 2005).
Zhao et al., An Integrated View of Copy Number and Allelic Alterations in the Cancer Genome Using Single Nucleotide Polymorphism Arrays, Cancer Research, 64, p. 3060-3071 (May 1, 2004).
European Examination Report in 08 742 125.1 dated Feb. 12, 2010.

Extended European Search Report in 06 838 311.6 dated Dec. 30, 2008.
International Preliminary Report on Patentability based on PCT/US2006/045281 dated May 27, 2008.
International Search Report based on PCT/US2006/045281 dated Sep. 28, 2007.
International Search Report based on PCT/US2008/003547 dated Apr. 15, 2009.
International Search Report based on PCT/US2009/034506 dated Jul. 8, 2009.
International Search Report based on PCT/US2009/045335 dated Jul. 27, 2009.
International Search Report based on PCT/US2009/052730 dated Sep. 28, 2009.
Office Action in U.S. Appl. No. 11/496,982 mailed May 27, 2010.
Office Action in U.S. Appl. No. 11/603,406 mailed Aug. 19, 2010.
Office Action in U.S. Appl. No. 11/634,550 mailed Aug. 4, 2010.
Office Action in U.S. Appl. No. 12/076,348 mailed Aug. 20, 2010.
Chu et al., "Statistical Model for Whole Genome Sequencing and its Application to Minimally Invasive Diagnosis of Fetal Genetic Disease," *Bioinformatics*, 25(10), p. 1244-1250 (May 15, 2009).
Daruwala et al., "A Versatile Statistical Analysis Algorithm to Detect Genome Copy Number Variation," *Proceedings of the National Academy of Science*, 101(46), p. 16292-16297 (Nov. 16, 2004).
Nannya et al., "A Robust Algorithm for Copy Number Detection Using High-density Oligonucleotide Single Nucleotide Polymorphism Genotyping Arrays," *Cancer Research*, 65(14), p. 6071-6079 (Jul. 15, 2005).
Perry et al., "The Fine-Scale and Complex Architecture of Human Copy-Number Variation," *The American Journal of Human Genetics*, 82(3), p. 685-695 (Mar. 2008).
Pfaffl et al., "Relative Expression Software Tool (REST©) for Group-Wise Comparison and Statistical Analysis of Relative Expression Results in Real-Time PCR," *Nucleic Acids Research*, 30(9), p. 1-10 (May 1, 2002).
Sebat et al., "Strong Association of De Novo Copy Number Mutations with Autism," *Science*, 316, p. 445-449 (Apr. 20, 2007).
PCT International Search Report based on PCT/US2010/050824 dated Nov. 15, 2010.
Chiu et al., Non-Invasive Prenatal Assessment of Trisomy 21 by Multiplexed Maternal Plasma DNA Sequencing: Large Scale Validity Study, BMJ, 342(7790), p. 1-9 (Jan. 2011).
Chiu et al., Non-Invasive Prenatal Diagnosis by Single Molecule Counting Technologies, Trends in Genetics, 25(7), p. 324-331 (Jul. 2009).
Dhallan et al., A Non-Invasive Test for Prenatal Diagnosis Based on Fetal DNA Present in Maternal Blood: A Preliminary Study, Lancet, 369(9560), p. 474-481 (Feb. 2007).
Ehrich et al., Noninvasive Detection of Fetal Trisomy 21 by Sequencing of DNA in Maternal Blood: A Study in a Clinical Setting, AJOG, 204(3), p. 205.e1-205.e11 (Mar. 2011).
Fan et al., Noninvasive Diagnosis of Fetal Aneuploidy by Shotgun Sequencing DNA from Maternal Blood, PNAS, 105(42), p. 16266-16271 (Oct. 2008).
Liao et al., Targeted Massively Parallel Sequencing of Maternal Plasma DNA Permits Efficient and Unbiased Detection of Fetal Alleles, Clin Chem, 57(1), p. 92-101 (Jan. 2011).
Lo et al., Plasma Placental RNA Allelic Ratio Permits Noninvasive Prenatal Chromosomal Aneuploidy Detection, Nature Medicine, 13(2), p. 218-223 (Feb. 2007).
Lo et al., Maternal Plasma DNA Sequencing Reveals the Genome-Wide Genetic and Mutational Profile of the Fetus, Science Translational Medicine, 2(61), p. 1-13 (Dec. 2010).
Lun et al., Noninvasive Prenatal Diagnosis of Monogenic Diseases by Digital Size Selection and Relative Mutation Dosage on DNA in Maternal Plasma, PNAS, 105(50), p. 19920-19925 (Dec. 2008).
Porreca et al., Multiplex Amplification of Large Sets of Human Exons, Nature Methods, 4(11), p. 931-936 (Oct. 2007).
Tsui et al., Non-Invasive Prenatal Detection of Fetal Trisomy 18 by RNA-SNP Allelic Ratio Analysis Using Maternal Plasma *SERPINB2* mRNA: A Feasibility Study, Prenatal Diagnosis, 29(11), p. 1031-1037 (Nov. 2009).
Turner et al., Massively Parallel Exon Capture and Library-Free Resequencing Across 16 Genomes, Nature Methods, 6(5), p. 315-316 (Apr. 2009).
Office Action in U.S. Appl. No. 11/496,982 mailed Jan. 21, 2011.
Office Action in U.S. Appl. No. 11/634,550 mailed Jan. 24, 2011.
Office Action in U.S. Appl. No. 11/603,406 mailed Feb. 18, 2011.
Office Action in U.S. Appl. No. 12/076,348 mailed Mar. 4, 2011.

* cited by examiner

| PATIENT ID | PATIENT FNAME | PATIENT LNAME | PATIENT DOB | PATIENT SEX | ... | DATE CREATED |
|---|---|---|---|---|---|---|
| 1 | Jim | Clark | 7/17/1967 | M | | 8/4/2004 |

Figure 2a: Table "Patient"

| PATIENT ID | PARAMETER ID | PARAMETER VALUE | ... | DATE CREATED |
|---|---|---|---|---|
| 1 | 1000 | 50 | | 8/4/2004 |

Figure 2b: Table "Measurement"

| PARAMETER ID | PARAMETER NAME | UNIT | ... | STANDARD | DATE CREATED |
|---|---|---|---|---|---|
| 1000 | Plasma HIV RNA Level | Copies/ml | | LOINC | 8/4/2004 |

Figure 2c: Table "Measurement Parameters"

FIG 2

| Regimen | Drugs | Monitoring |
|---|---|---|
| 2 | Zidovudine (AZT); Didanosine (DDI); Lopinavir and Ritonavir (Kaletra ®) | CD4 (baseline & 6-monthly); FBC (baseline, 1, 3 and 6, 6-monthly thereafter); fasting cholesterol and triglycerides (baseline only) |
| TB | For use in patients on regimen 2 who develop TB during ART: Saqinavir and Ritonavir (in place of Lopinavir and Ritonavir) | As above |

Fig 3a: An excerpt of WHO Guidelines on ART combinations

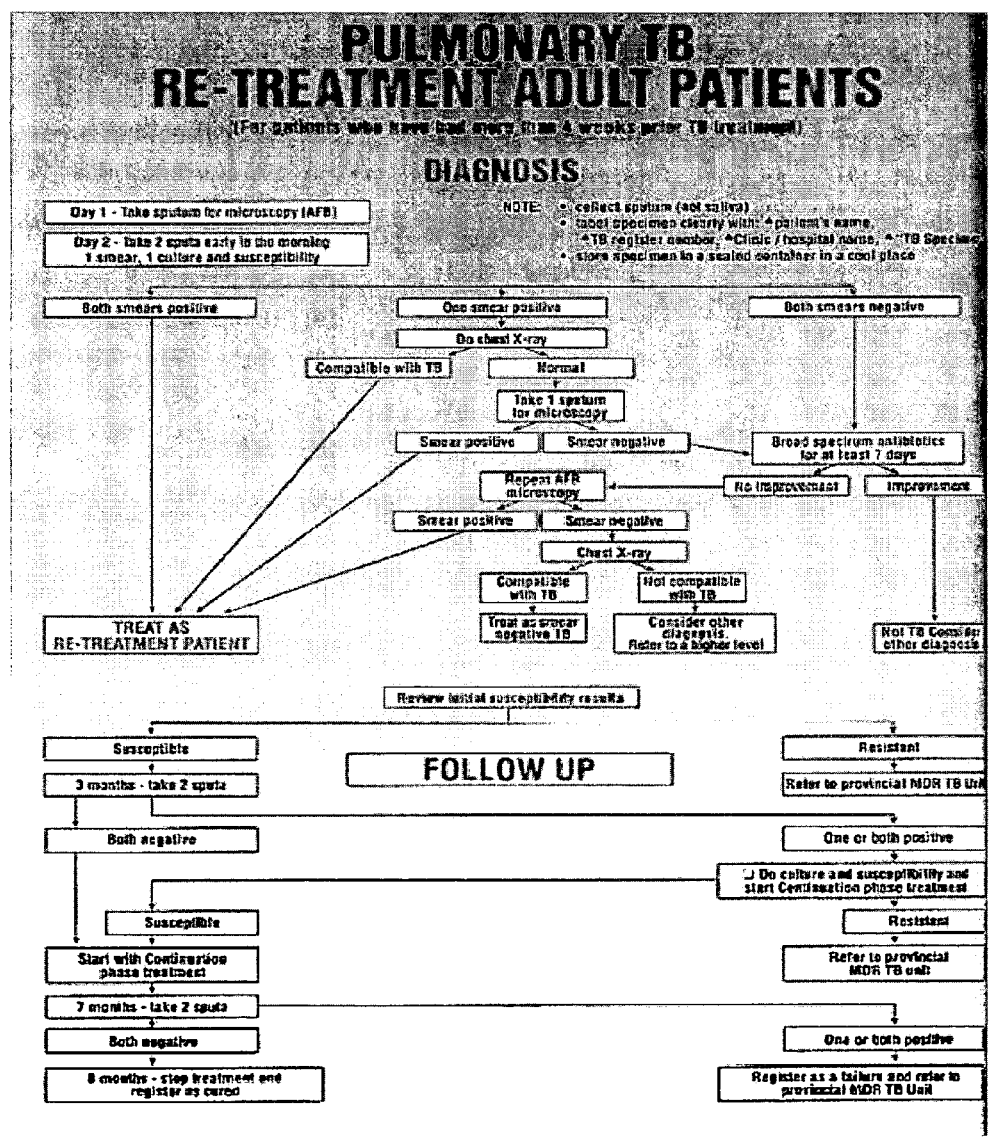

Fig 3b: An excerpt from Guidelines for Managing TB Patients

FIG 3

|   |   |   |   |   |   |   |   |   |
|---|---|---|---|---|---|---|---|---|
| Toolbar | | | | | | | | |
| Section 1 (1200) | | | | | | | | |
| Patient Name 1201 | | | Serch Criteria 1205 | | | | | |
| Patient Number 1202 | | | Search Criteria 1206 | | | | | |
| Current Date 1203 | | | Genotype Information 1207 | | | | | |
| Notes 1204 | | | Phenotype Information 1208 | | | | | 1209 |
| Section 2 (1219) | | | | | | | | |
| 1220 | 1221 | 1222 | 1223 | 1224 | 1225 | 1226 | 1227 | 1228 |
| 1220 | 1221 | 1222 | 1223 | 1224 | 1225 | 1226 | 1227 | 1228 |
| 1220 | 1221 | 1222 | 1223 | 1224 | 1225 | 1226 | 1227 | 1228 |
| 1220 | 1221 | 1222 | 1223 | 1224 | 1225 | 1226 | 1227 | 1228 |
| 1220 | 1221 | 1222 | 1223 | 1224 | 1225 | 1226 | 1227 | 1228 |
| 1220 | 1221 | 1222 | 1223 | 1224 | 1225 | 1226 | 1227 | 1228 |
| Section 3 (129) | | | | | | | | |
| 1230 | | | 1233 | | | | 1236 | |
| 1231 | | | 1234 | | | | 1237 | |
| 1232 | | | 1235 | | | | | |

FIG 12

SYSTEM AND METHOD FOR IMPROVING CLINICAL DECISIONS BY AGGREGATING, VALIDATING AND ANALYSING GENETIC AND PHENOTYPIC DATA

CROSS-REFERENCES TO RELATED APPLICATIONS

This application claims priority under 35 U.S.C. §119(e) to U.S. Provisional Application No. 60/607506, "System and Method for Improving Clinical Decisions by Aggregating, Validating and Analyzing Genetic and Phenotypic Data" by Matthew Rabinowitz, Wayne Chambliss, John Croswell, and Miro Sarbaev, filed Sep. 7, 2004, the disclosure of which is incorporated by reference herein in its entirety.

BACKGROUND OF THE INVENTION

1. Field of the Invention

The invention relates generally to the field of analyzing, managing and acting upon clinical information, and specifically to a system which integrates genetic and phenotypic data from a group of subjects into a standardized format in order to validate the data and to make better decisions related to the genetic and phenotypic information of a particular subject.

2. Description of the Related Art

The current methods by which clinical decisions are made do not make the best possible use of existing information management technologies. Very little data from clinical trials and electronic clinical records—collected as it is by a variety of methods, and stored in many different formats across a wide range of systems—is immediately reusable by other groups in the biomedical community and can be accessed to aid caregivers and other decision makers. This situation will become considerably more complicated once personal genetic data occupies a more central role in understanding the causes and treatments of diseases and other predispositions of subjects. Within the next decade it will be possible to scan the entire genome of a patient either for clinical trials, or for the purpose of personalized drug assignment. Insofar as researchers continue to use different methods and systems for storing and analyzing this data, and the associated phenotypic data, all of the difficulties associated with sharing information within the biomedical community will persist and worsen.

A body of prior art exists to develop tools that manage the integration of existing data sets. For example, success has been achieved with tools that input textual data and generate standardized terminology in order to achieve information integration such as, for example, the Unified Medical Language System (UMLS): Integration Biomedical Terminology. Tools have been developed to inhale data into new ontologies from specific legacy systems, using object definitions and Extensible Markup Language (XML) to interface between the data model and the data source, and to validate the integrity of the data inhaled into the new data model. Bayesian classification schemes such as MAGIC (Multisource Association of Genes by Integration of Clusters) have been created to integrate information from multiple sources into a single normative framework, using expert knowledge about the reliability of each source. Several commercial enterprises are also working on techniques to leverage information across different platforms. For example, Expert Health Data Programming provides the Vitalnet software for linking and disseminating health data sets; CCS Informatics provides the eLoader software which automates loading data into ORACLE® Clinical; PPD Patient Profiles enables visualization of key patient data from clinical trials; and TABLE-TRANS® enables specification of data transformations graphically.

Depending on the tool, automated approaches to data integration can be far less resource intensive than the manual data integration, but will always be more constrained. It is exceedingly difficult to teach a computer how data of heterogeneous types should be sensibly merged. Prior art that most successfully approaches data integration makes use, in some form, of standardized master templates which define a data model, and provide a clear framework to researchers for inputs into, and augmentations of, that data model. This has been successfully applied, for example, in the GO (Gene Data model) project which provides a taxonomy of concepts and their attributes for annotating gene products. Similar projects include the Mouse Gene Database (MGD) and the Mouse Gene Expression Database (GXD). However, no system exists today to combine all phenotypic and genetic information associated with a patient into a single data model; to create a series of logical and statistical interrelationships between the data classes of that standard; to continually upgrade those relationships based on the data from multiple subjects and from different databases; and to use that information to make better decisions for an individual subject.

Prior art exists to manage information in support of caregivers and for streamlining clinical trials. Some of the enterprises involved in this space include Clinsource which specializes in software for electronic data capture, web randomization and online data management in clinical trials; Perceptive Informatics which specializes in electronic data capture systems, voice response systems, and web portal technologies for managing the back end information flow for a trial; and First Genetic Trust which has created a genetic bank that enables medical researchers to generate and manage genetic and medical information, and that enables patients to manage the privacy and confidentiality of their genetic information while participating in genetic research. None of these systems make use of expert and statistical relationships between data classes in a standardized data model in order to validate data or make predictions; or provide a mechanism by which electronically published rules and statistical models can be automatically input for validating data or making predictions; or guarantee strict compliance with data privacy standards by verifying the identity of the person accessing the data with biometric authentication; or associate all clinical data with a validator the performance of which is monitored so that the reliability of data from each independent source can be efficiently monitored; or allow for compensation of individuals for the use of their data; or allow for compensation of validators for the validation of that data.

Prior art exists in predictive genomics, which tries to understand the precise functions of proteins, RNA and DNA so that phenotypic predictions can be made based on genotype. Canonical techniques focus on the function of Single-Nucleotide Polymorphisms (SNP); but more advanced methods are being brought to bear on multi-factorial phenotypic features. These methods include regression analysis techniques for sparse data sets, as is typical of genetic data, which apply additional constraints on the regression parameters so that a meaningful set of parameters can be resolved even when the data is underdetermined. Other prior art applies principal component analysis to extract information from undetermined data sets. Recent prior art, termed logical regression, also describes methods to search for different logical interrelationships between categorical independent variables in order to model a variable that depends on interactions between multiple independent variables related to genetic data. However, all of these methods have substantial shortcomings in the realm of making predictions based on genetic and phenotypic data. None of the methods provide an effective means of extracting the most simple and intelligible rules from the data, by exploring a wide array of terms that are designed to model a wide range of possible interactions of variables related to genetic data. In addition, none of these prior techniques enable the extraction of the most simple intelligible rules from the data in the context of logistic regression, which models the outcome of a categorical variable using maximum a-posteriori likelihood techniques, without making the simplifying assumption of normally distributed data. These shortcomings are critical in the context of predicting outcomes based on the analysis of vast amounts of data classes relating to genetic and phenotypic information. They do not effectively empower individuals to ask questions about the likelihood of particular phenotypic features given genotype, or about the likelihood of particular phenotypic features in an offspring given the genotypic features of the parents.

SUMMARY OF THE INVENTION

The information management system disclosed enables the secure integration, management and analysis of phenotypic and genetic information from multiple subjects, at distributed facilities, for the purpose of validating data and making predictions for particular subjects. While the disclosure focuses on human subjects, and more specifically on patients in a clinical setting, it should be noted that the methods disclosed apply to the phenotypic and genetic data for a range of organisms. The invention addresses the shortcomings of prior art that are discussed above. In the invention, a standardized data model is constructed from a plurality of data classes that store patient information including one or more of the following sets of information: patient profile and administrative information, patient symptomatic information, patient diagnostic information, patient treatment information, and patient's genetic information. In one embodiment of this aspect of the invention, data from other systems is converted into data according to the standardized data model using a data parser. In the invention, relationships are stored between the plurality of data classes in the standardized data model. In one embodiment, these relationships are based on expert information. The relationships between the data classes based on expert information may one or more of the following types: integrity rules, best practice rules, or statistical models that may be associated with numerical parameters that are computed based on the aggregated data. In one embodiment, the statistical models are associated with a first data class, and describe the plurality of relevant data classes that should be used to statistically model said first data class. In one embodiment of the invention, the statistical and expert rules pertaining to the standardized data classes are automatically inhaled from electronic data that is published according to a standardized template.

In another aspect of the invention, methods are described for extracting the most simple and most generalized statistical rules from the data, by exploring a wide array of terms that model a wide range of possible interactions of the data classes. In one embodiment of this aspect of the invention, a method is described for determining the most simple set of regression parameters to match the data in the context of logistic regression, which models the outcome of a categorical variable using maximum a-posteriori likelihood techniques, without making the simplifying assumption of normally distributed data.

In another aspect of the invention, a method is described for addressing questions about the likelihood of particular phenotypic features in an offspring given the genotypic features of the parents.

In another aspect of the invention, for each user of the system is stored a biometric identifier that is used to authenticate the identity of said user, and to determine access privileges of said user to the data classes. In this aspect of the invention, each data class is associated with data-level access privileges and functional-level access privileges. These access privileges provide the ability for records to be accessed in a manner that does not violate the privacy rights of the individuals involved so that research can be performed on aggregated records, and so that individuals whose information satisfies certain criteria can be identified and contacted.

In another aspect of the invention, each data class in the system is associated with one or several validators, which are the entities who validated the accuracy of the information in that class. In this embodiment, data associated with the validator enables users to gauge the level of reliability of the validated information. In one embodiment of this aspect of the invention, the system provides a method by which individuals can be compensated for the use of their data, and validators can be compensated for the validation of that data.

BRIEF DESCRIPTION OF THE DRAWINGS

FIG. 2 illustrates examples of the data schema according to which the data model of the invention can be implemented.

FIG. 3 illustrates an example set of best practice guidelines that can be inhaled into the standardized ontology to validate inhaled data and proposed interventions.

FIG. 12 illustrates a conceptual graphical user interface by which a caregiver may interact with the system to see the outcome predictions for a particular patient subjected to a particular intervention, according to each of the statistical models of various experts.

DETAILED DESCRIPTION OF THE PREFERRED EMBODIMENT

Figure 1:
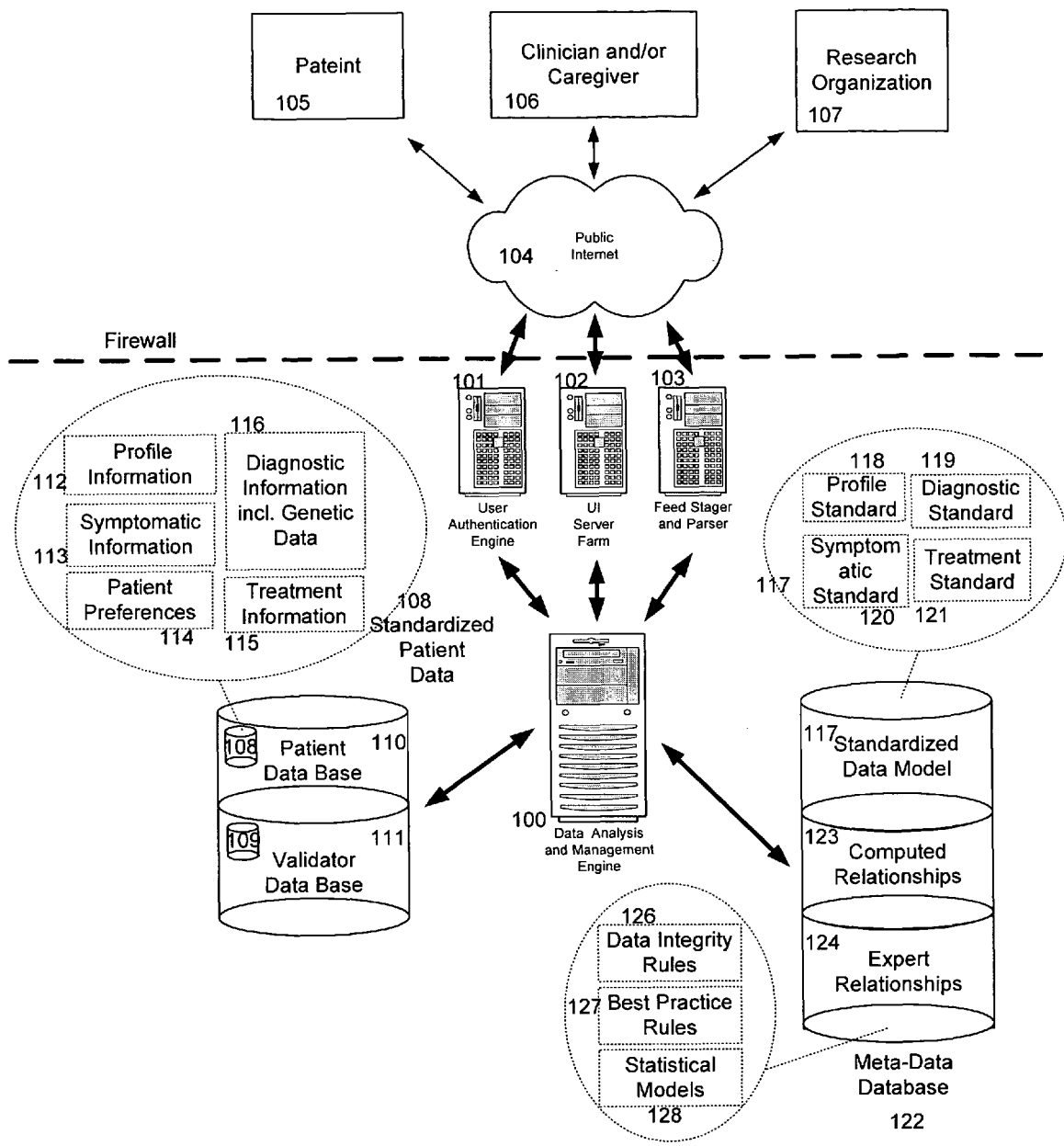
FIG. 1 illustrates an overview of a system in which the present invention is implemented.

Functional Overview of the System
Description of System Functionality

Assume in this discussion that the subjects are human patients in a clinical setting. A primary goal of the disclosed system is to enable clinicians to make better, faster, decisions using aggregated genetic and phenotypic data. In order to accomplish this, a secondary goal must be achieved, namely to enable research organizations to integrate and validate genetic and phenotypic data from multiple heterogeneous data sources. In a preferred embodiment, these two objectives are achieved with a system that has the following functionality: i) genetic, clinical and laboratory data are integrated into a standardized data model; ii) the integrity of information input into the data model is validated by a set of expert-rule based relationships and statistical relationships created between the data classes of the data model; iii) when data fails validation, the system facilitates remote upgrading of the data by data managers via a secure architecture; iv) clinicians are enabled by the system to subject the data of their patients to the models and methods of other researchers in order to have a meaningful prediction of clinical outcome; v) statistical relationships between data classes within the data model are refined based on the validated data that is input into the data model; vi) statistical models are selected to make the most accurate statistical predictions for data classes within the data model with the highest degree of confidence based on validated data within the data model; viii) statistical models are designed to make more accurate predictions correlating sparse genetic data with phenotypic data.

Integrating Clinical and Genetic data into a Standardized Data Model

The system disclosed makes clinical treatment, clinical trial and laboratory data useful to distributed organizations by inhaling the information into a format that has unambiguous definitions and by enabling contributions from different database systems. The data model consists of data classes that encompass the full range of patient profile, symptomatic, intervention, diagnostic and genetic information. In one embodiment, these data classes are composed from a set of emerging standards, including: The SNOMED Clinical Terms (CT) standard which enables a consistent way of indexing, storing and understanding clinical data; the Logical Observation Identifiers Names and Codes (LOINC) standard for all clinical and laboratory measurements; the Health Level 7 (HL7) standard which focuses on data processes and messaging; National Drug File Reference Terminology (NDF-RT) which provides standard terminology for drugs; and the FASTA format for representing genetic data. In one embodiment, the data classes in the standardized model are based on the Unified Medical Language System Metathesaurus developed by the National Library of Medicine, which integrates multiple emerging standards into one data ontology. Many of the illustrative examples in this disclosure relate to integrating data of HIV/AIDS patients for the purpose of improving selection of anti-retroviral therapies (ART). This data serves as a good illustration of the functionality of our system because health care in developed and developing nations would be enhanced by a system that aggregates HIV/AIDS genetic and phenotypic data as it becomes available to identify the best drug combinations for different mutations and strains of the HIV/AIDS virus.

Integrity, Best-Practice and Statistical Relationships

The standardized data model is made useful by relationships that will be created between standardized data classes. The relationships will be of three types: i) data integrity relationships ii) best practice relationships, and iii) statistical relationships. The data integrity relationships will be expert rules that check for clear errors and inconsistencies in the data. For example, such rules would include checking that laboratory CD4+ lymphocyte counts and viral load counts are within reasonable ranges, or checking that a particular genetic sequence is not from a contaminated Polymerase Chain Reaction (PCR) by checking against other samples from the same laboratory to ensure they are not too closely correlated. Best practice relationships will be expert rules that describe correct methods for data collection and for clinical interventions. For example, such rules would include the requisite laboratory tests to establish that a patient requires Anti-Retroviral Therapy (ART), or rules describing which ART drugs should and should not be used together. Statistical relationships between data classes will be created by inhaling models created by experts, and continually refining the parameters of the models by aggregating patient data inhaled and validated in the standardized data model. In one embodiment, for each data class to be modeled, the system will inhale multiple different statistical models and choose from amongst them that which is best suited to the data—this will be described later. In a preferred embodiment, as the data is inhaled, it is checked for errors, inconsistencies and omissions by a three step process. The three steps will correspond respectively to checks for violation of the data integrity relationships, the best practice relationships and the statistical relationships.

Applying Expert Knowledge in the Data Model Across Multiple Client Systems

In a preferred embodiment, the system is architected so that a limited subset of validation rules will check the integrity of the data at the time of parsing the data from the client database, before it enters the standardized data model. These client-system-dependent rules must be developed specifically for each client database in a specialized cartridge. For scalability, the cartridge size and complexity will be kept to a minimum. The majority of data validation will occur once data is inhaled into the data model. In this way, the relationships encoded into the standardized data model can be applied to validating a wide range of client databases, without having to be reconfigured for each client system. In addition, the previously validated data will be used to the refine statistical rules within the data model. In this way, new patient data from other client systems can be efficiently inhaled into the standardized data model.

Using an Automatic Notification System to Upgrade Invalid Data

When data fails the validation process described above, the system will, in a preferred embodiment, generate an automatic notification for the relevant data manager. In a preferred embodiment, an embedded web-link in this notification will link to a secure URL that can be used by the data manager to update and correct the information. The validation failure, whether based on integrity relationships, the best-practice relationships, or the statistical relationships, generates a human-readable explanatory text message. This will streamline the process of integrating data from multiple collaborating institutions and reduce data errors.

Enabling Updates to the Standardized Data Model

As upgrades to data standards are made, the standardized data model will need to be upgraded while preserving both the relationships between data classes and the validity of data formatted according to the affected standards. In a preferred embodiment, the standardized data model will uses a flex schema where possible (described below) for the standardized data model. While inefficient for queries, the flex schema will enable straightforward upgrades of the data model to accommodate evolving standards. In a preferred embodiment, a parsing tool will translate data from one version of the data model to another and will appropriately upgrade relationships between data classes based on a mapping between the old and the updated data classes. Where such mappings are not possible without further data or human input, automatic notifications will be generated for the data managers. If no mechanism can enable translation, affected patient data will be replaced by a pointer to the data in the old standardized data model. Upon completion of the data model upgrade, the re-validation of all updated data records will then be performed and should generate the same results. In addition, statistical analysis of the updated records will be re-computed to verify that the same set of outcomes is generated.

Enabling Clinicians to Subject the Data of their Patients to the Models and Methods of other Researchers In one embodiment, the system will enable physicians to analyze their own patient's genetic and phenotypic data using the methods and algorithms of other researchers. This will enable physicians to gain knowledge from other collaborators, and will provide a streamlined validation of the results generated by clinical studies. A clinical study can typically be broken into three information modules: namely i) the clinical data, ii) the statistical model used, iii) and the statistical results. A template will be created to enable researchers to specify both their data and their statistical models, or the functions they use to act on that data. Researchers will use the template to specify two function types: a training function and a mapping function. The training function will input training data as dependent and independent variables, and will output the set of parameters required to map between them according to the model.

The mapping function will input the independent variables, and the parameters, and will generate a prediction of the dependent variable as well as a confidence measure with which the prediction is made. These functions may be defined using off-the-shelf software such as SAS or MATLAB.

In one embodiment, when a clinical study is published electronically according to the template, the clinical data for that trial and the model used to analyze that data will be automatically inhaled into the database. The statistical results will then be regenerated and checked for agreement with those published. Parameters that constitute the statistical model (such as regression parameters) will be recomputed, and refined as new relevant data is inhaled into the standardized database. An interface will be created for a physician to generate a clinical prediction for his own patient's data by applying the model of a chosen clinical study.

Technical Description of System

Creating the Standardized Data Model 117 based on Existing Standards

FIG. 1 provides an overview of the system architecture according to a preferred embodiment. The patient data base 110 contains standardized patient data 108. In a preferred embodiment, the data classes will encompass: patient profile information (112); patient symptomatic information (113); patient diagnostic information (116); and patient treatment information (115). The specific information describing each data class within each category is defined in the standardized data model 117 in the meta-data database 122. In a preferred embodiment, the defined standards will include a patient profile standard 118, a diagnostic standard 119, a symptomatic standard 120 and a treatment standard 121.

In a preferred embodiment, the patient profile standard 118, the diagnostic standard 119, the symptomatic standard 120 and the treatment standard 121 consist of data classes that are leveraged from the following emerging standards for clinical and laboratory data and protocols for data exchange:

Systematized Nomenclature of Medicine Clinical Terms (SNOMED-CT): Based on a terminology developed by the College of American Pathology and the United Kingdom National Health Service's Read Codes for general medicine, SNOMED-CT is the most comprehensive clinical ontology in the world. It contains over 357,000 health care concepts with unique meanings and logic-based definitions organized in hierarchies, and can be mapped to the existing International Classification of Disease $9^{th}$ Revision—Clinical Modification. Through a licensing agreement with the National Library of Medicine, SNOMED-CT is available through the Unified Medical Language System Metathesaurus and is considered an essential component of President George Bush's ten year plan to create a national health information technology infrastructure (including electronic health records) for all Americans.

Logical Observation Identifiers Names and Codes (LOINC): Developed by the Regrienstreif Institute at the Indiana University School of Medicine, the LOINC laboratory terms set provides a standard set of universal names and codes for identifying individual laboratory and clinical results, allowing developers to avoid costly mapping efforts for multiple systems.

Health Level 7 (HL7) version 3.0: HL7 is the primary messaging standard for sharing healthcare information between clinical information systems supported by every major medical informatics vendor in the United States. In a preferred embodiment, the data in the standardized ontology will be exchangeable using HL7 compliant messaging.

RxNorm: RxNorm is a clinical drug nomenclature developed jointly by the National Library of Medicine, the Food and Drug Administration, Veterans Administration, and Health Level 7. The ontology includes information about generic and brand names, drug components, drug strength, and the National Drug Codes.

Fasta/Blast: The Fasta and Blast algorithms are heuristic approximations of the Smith-Waterman algorithm for sequence alignment. Widely used for genetic sequence similarity analysis, the standardized database will utilize the readily sharable Fasta format to represent sequence information.

In one embodiment, the data classes of the standardized ontology are based on the data class definitions provided by the UMLS Metathesaurus managed by the National Library of Medicine.

Representation Patient Data 108 according to the Standardized Data Model 117

A static/flex approach will be used in the database to represent data entities of the standardized patient data 108. This approach balances the desire to have a data schema that is easy to read and tune for performance, versus a schema that supports flexibility in data representation. The static schema will define the non-volatile entities in the standardized patient data 108 and their associated attributes. Data that is called upon frequently in queries, unlikely to evolve with standards, and/or essential to system function will be modeled in this static schema. FIG. 2a illustrates part of a table in the standardized patient data 108 configured according to the static schema for the entity "Patient". In this data schema, the columns in the data tables in the patient database 110 are pre-defined, and data is entered directly into these pre-defined columns. Although this scheme is easy to query, changes in this schema are problematic—they involve adding columns and/or tables, and rewriting code for data retrieval. Consequently, the majority of the patient data 108 will be stored according to the flex schema. In this scheme, the standardized data model 117 describes a layer of metadata, or data about data. The flex schema will be used to store all standardized patient data 108 that may be volatile. This will include data that is unique to a specialized medical scenario and is not in an accepted standard, and/or data in a standard that may evolve. FIG. 2b and FIG. 2c illustrate a flex schema for storing laboratory measurements of HIV viral load. FIG. 2b illustrates the table that is part of the standardized patient data 108. FIG. 2c illustrates the table that is in the standardized data model 117. Although this schema is more complex, and slower to query, the addition of a measured parameter entity to the standardized patient data 117 does not require any new tables/columns. In a preferred embodiment, wherever feasible from the perspective of system performance, the database will use a flex schema for each entity in the standardized patient data so that upgrades to the data standards can be easily accommodated.

The data model will address the full range of entities that relate to i) patient profile—an individual's demographic and psychographic information; ii) clinical presentation; iii) treatment history; iv) diagnostic information; and v) genomic data. In a preferred embodiment, the latter will include both human genetic profile such as host genetic factors that may influence resistance as well as genetic data on any infectious agents, such as viral genomic data that relates to the patient's strain-of-infection. A unique identifier, compliant with the Health Insurance Portability and Accountability Act (HIPAA), will be used to link to other entities in the data model. In a preferred embodiment, all data representation and access will be HIPAA compliant.

Relationships between the Data Classes

A key element that makes the standardized data model unique and valuable is the set of relationships that exist between the data classes in the standardized data model 117. These relationships can be divided into computed statistical relationships 123 and expert relationships 124. Expert relationships are discussed first. In a preferred embodiment, three types of expert relationship are implemented—integrity rules, best practice rules, and statistical models.

Integrity rules: The integrity rules are algorithms for checking the data based on heuristics described by domain experts. In a preferred embodiment, each integrity relationship is implemented as a software function that inputs certain elements of the patient data record, and outputs a message indicating success or failure in validation. Simple integrity functions include checking that all key data fields, such as a patient's last name or baseline CD4+ cell count, are present in the patient data record; confirming the market availability of a drug mentioned in the patient treatment record. More complex integrity functions include assessing the possibility of laboratory cross-contamination of a viral genotype PCR sample by aligning a new sequence and correlating it with other sequences generated from the same laboratory at the same time period; ensuring that samples aren't misnamed by comparing each sequence from an individual with previous samples from that individual to ensure they are not too dissimilar; and ensuring that a gene sequence itself is valid by checking for unexpected stop codons, frame shifts, and unusual residues.

Best practice rules: These will encode guidelines for collecting patient data, and for clinical patient management. In a preferred embodiment, these will be stored in the meta-data database 122 as best practice rules 127. Two examples of best practice guidelines are illustrated in FIG. 3. FIG. 3a is the recommendation for administration of a second regimen of ART drugs for patients with and without Tuberculosis (TB), according to United Nations World Health Organization (WHO) guidelines. The best practice rules 127 are typically more complex than the excerpt shown. ART guidelines, for example, would include such considerations as: not using two anti-retroviral medications of the same nucleoside due to the potential for cross-resistance, nor using two medications that have the same side effect profile. The best practice rules 127 will be encoded using the data classes defined in the standardized data model 117. The best practice code, acting on the standardized data for a particular patient 108, will be able to determine the context (e.g. HIV/AIDS patient on regimen 2, any decisions that need to be taken, for example whether or not a patient has TB, and any actions that should be, or should have been, taken (e.g. replacing Saqinavir with Lopinavir). FIG. 3b shows another example set of guidelines in a flow-diagram form. In a preferred embodiment, guidelines such as these are encoded into the best practice rules 127 in the meta-data database 122, acting on the standardized data model 117, in order to determine context, decisions and actions for particular patient's standardized data 108.

Figure 4:
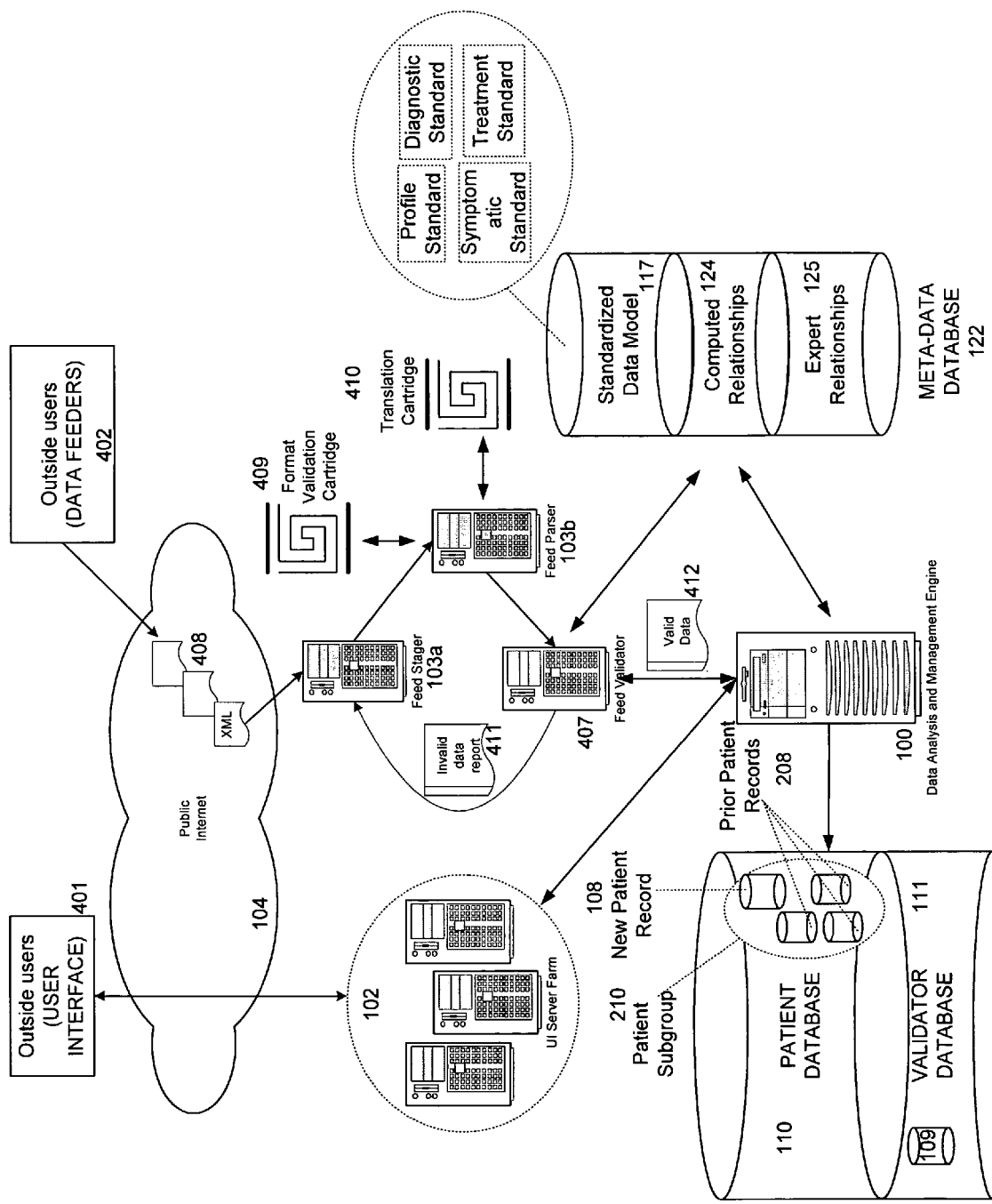
FIG. 4 illustrates an architecture by which data can be inhaled into the standardized data model and validated.

Statistical models: Statistical models 128 will be stored in the meta-data database 122. The use of the statistical models 128 for prediction of clinical outcome for clinicians will be further elaborated below and is described in FIG. 4. The statistical models 128 will also be used for data validation. The statistical models will describe how to calculate the likelihood of data in a particular patient record 108 in the patient data database 110, given data about prior patients 208 (FIG. 4) with similar characteristics—termed the patient subgroup 210 (FIG. 4). In a preferred embodiment, the statistical model will contain a set of parameters which will be stored as part of the computed relationships data 123 of the meta-data database 122. Each of the statistical models 128 will specify the subgroup 210 to which it applies so that the DAME 100 can evaluate data from a particular patient 108 against the data for all other patients in that subgroup 208. Each data class in the patient record can be represented with a random variable, $X_{f,n}$, which describes feature f of patient n. This data could come from the patient profile information 112, symptomatic information 113, treatment information 115, or diagnostic and genetic information 116, and may be a continuous or categorical variable. In a preferred embodiment, some of the statistical models 128 are regression models of one or more variables. For example, the variable of interest, $Y_n$, could be the log of the CD4+ cell count of patient n, and the relevant subgroup 210 could be all patients who have received ART for more than 6 months without a resistant viral strain. The DAME could then compare datum $Y_{N+1}$ associated with the record 108 of a patient N+1, and determine whether or not it is reasonable. In the simplest regression model, the DAME 100 evaluates $Y_{N+1}$ based on the sample mean and variance of $Y_n$ over the subgroup 210 of N patients. In a more complex model, the DAME 100 uses a regression model involving multiple variables to represent the dependent variable:

$$Y_n = \beta_0 + \sum_{p=1}^{P-1} \beta_p f_p(\vec{X}_n) + \varepsilon_n$$

where $\varepsilon_n$ is the error term, $\beta_p$ is the $p^{th}$ regression parameter, $f_p$ is a function of the independent variables, and $\vec{X}_n$ is the vector of relevant features for patient n. These independent variables may include such attributes as ART dosage, baseline CD4+ cell count and viral load, treatment adherence, diet, viral genetic mutations, and human genetic alleles. To simplify, all the functions of the independent variables may be represented as a matrix $X_n=[1f_1(\vec{X}_n) \ldots f_p(\vec{X}_n)]$ and the DAME may estimate $\hat{Y}_{N+1}=X_{N+1}b$ where b is the vector of estimated regression parameters. In one embodiment, a threshold or margin for $Y_{N+1}$ is estimated with some confidence bound of $1-\alpha$, meaning that there is a probability of $1-\alpha$ that $Y_{N+1}$ will lie within that threshold. Assuming a probability of $\alpha$ that $Y_{N+1}$ will lie outside that range, the range is given by:

$$\hat{Y}_{N+1} \pm t\left(1-\frac{\alpha}{2}, N-P\right)s(\hat{Y}_{N+1}-Y_{N+1}),$$

where $$t\left(1-\frac{\alpha}{2}, N-P\right)$$

is a value where the cumulative Student-T distribution with N-P degrees of freedom is equal to $\alpha/2$: $F_{T,N-P}(t(1-\alpha/2, N-p))=\alpha/2$, and where $s(\hat{Y}_{N+1}-Y_{N+1})$ is an unbiased estimate of the covariance $\sigma(\hat{Y}_{N+1}-Y_{N+1})$ based on the N prior patient records 208 and computed using known techniques. If the actual value of $Y_{N+1}$ for the patient N+1 is outside of this range, the individual record 108 will be identified as potentially erroneous.

Data Acquisition, Validation and Integration

The preferred architecture for interfacing between external sources of data and the internal schemas of the underlying standardized database is shown in FIG. 4. In a preferred embodiment, the process of data acquisition begins with the data feeders 402, which send HL7-compliant XML-encoded data 408 through public Internet 104. Note that the data feeder 402 and user 401 could be the same entity in certain usage scenarios. XML files 408 are received by the feed stager 103a, which can be a secure FTP site, or any other data transfer protocol/messaging receiver server. Data is passed from the feed stager to the feed parser 103b, which parses both XML and non-XML encoded data. The feed parser 103b will input format validation cartridge 409 and translation cartridge 410 specifically adapted to the particular source of data. Importantly, the knowledge required for parsing and preliminary integrity checking by the feed parser 103b will be maintained externally to the parser in the cartridges 409, 410, which are effectively mini-databases and include no program code. Thus, the replaceable cartridges may be updated and enhanced without changing the code. These cartridges 409, 410 may be combined into a single cartridge.

The feed validator 407 will apply the relationships stored in the metadata database to the parsed data, assessing the data in terms of integrity rules 126, best practice rules 127, and statistical models 128 stored in the meta-data database 122. All relationships, including expert relationships 125 and computed relationships 124, will be stored along with human-readable text messages describing the relationships, or the underlying statistical model 128 in the case of computed relationships 124. Invalid data is sent back to the data source with a report 411 of data inconsistencies for correction, compiled using the human-readable messages. Valid data is sent to the data analysis and management engine (DAME) 100. The feed validator 407 may be partly implemented within the meta-data database 122 (expert relationships 125) or partly implemented as modules, residing outside the database, that communicate with the feed stager 103a and feed parser 103b.

The DAME 100 performs standard operations on validated data 112 (e.g. updating statistical counts) prior to insertion into the patient database 110. The patient database is standards-aware and compliant, conforming to the templates in the standardized data model 117 of the metadata database 122. In a preferred embodiment, the DAME 100, the feed validator 407, and feed parser 103b will be implemented as modules in an application server. These modules will then be utilized both by the user interface servers 102 and client-side applications to provide data input validation. In order to preserve data integrity in the path between feed stager 103a and the patient database 110, data is moved in transactional sets such as a patient record. If some data are invalidated within a transactional set (say a missing patient name field), the whole set is rolled back and rejected without the generation of orphan records.

In a preferred embodiment, each information provider 402 generates and maintains local unique numeric identifiers for supplied records (e.g. patient ID) and uses this identifier when updating previously submitted patient data.

Validator Database

In a preferred embodiment, the system also includes a validator database 111 in which information is stored about all external entities who validate, or verify the correctness of, patient data 108. In the preferred embodiment, each validator is identified by a unique ORGANIZATION_ID as described above. In a preferred embodiment, every element of a patient record 108 in the patient data base 110 is associated with some validator 109 which is the outside entity that validated that data. The validator may be the clinician that submitted patient symptomatic 113 or treatment information 115, or a laboratory that submitted genetic information 116. Whenever a new patient record is validated by the feed validator 807 and added to the patient database 110, the new data is associated with the particular validator 109 that validated that submitted the data. For each validator 109, a set of profile information is stored (such as the institution, relevant contact information etc.) together with a record of the number of data records that have failed validation, and why, as well as the number of records that have passed validation. In this way, each validator can be gauged in terms of their reliability. The more reliable the validator, the more reliable and valuable the data. It is also possible that if information is sold, that information is priced based on the reliability of the validator, in addition to the value of the data itself. This concept is particularly relevant in the context of individuals being solicited for their genetic and phenotypic information by academic and research institutes, drug companies and others.

Figure 5:
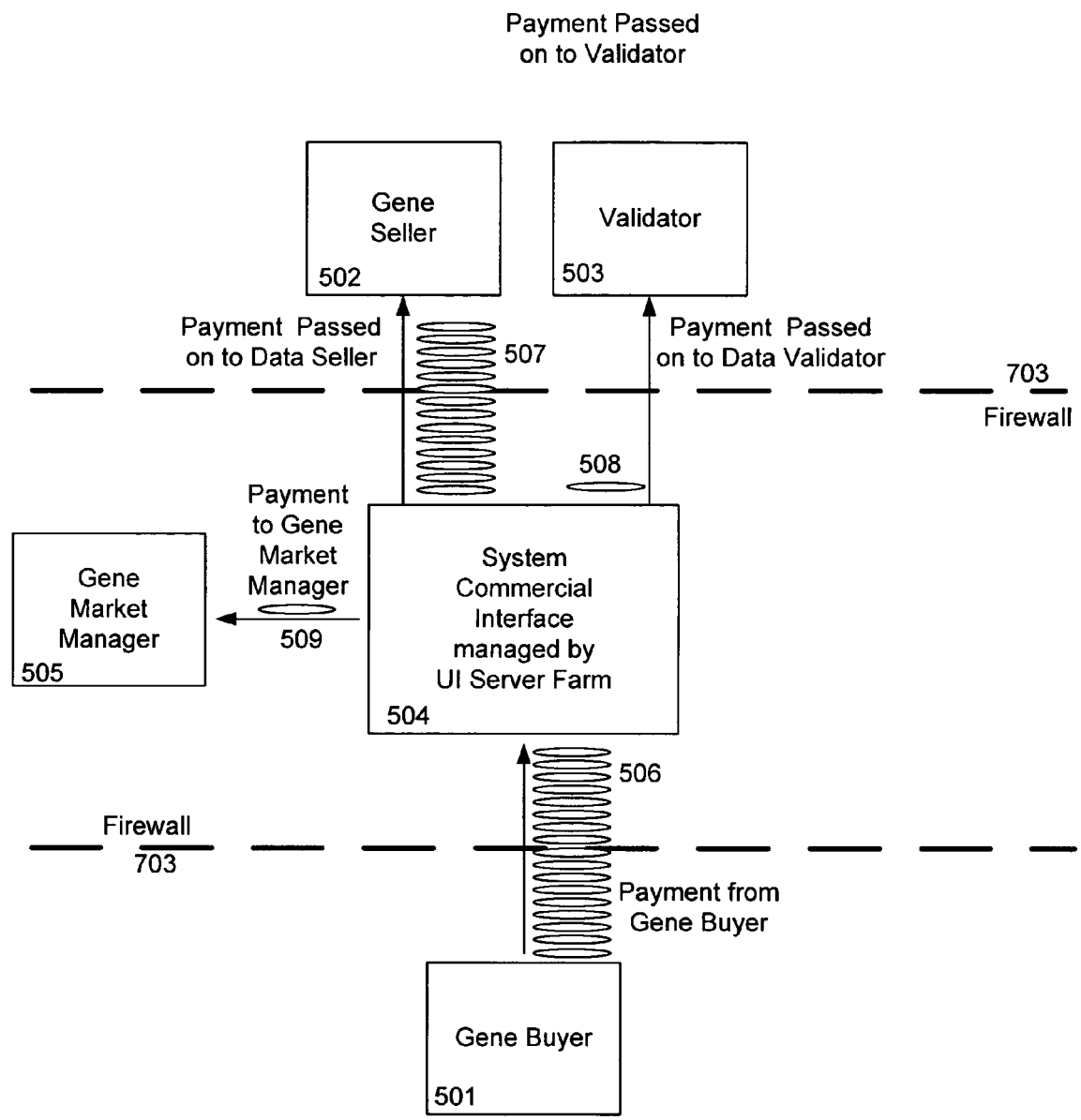
FIG. 5 describes a method for compensating seller, validator and market manager for the sale of genetic or phenotypic information using the disclosed system.

In one embodiment, illustrated in FIG. 5, the system has users 401 that are owners of valuable genetic and phenotypic information—gene sellers 502—as well as users 401 that are purchasers of genetic and phenotypic information—gene buyers 501. In this scenario, the gene buyer 501 can view the information of the gene seller 501 as rendered by the UI server farm 102 with all personal identifiers removed and compliant with HIPAA requirements. In one embodiment, an entity termed the gene market manager 505 is responsible for putting gene buyers 501 in touch with gene sellers 502 while preserving the privacy rights of both parties. The market manager 505 has access to the contact information of both buyers 501 and sellers 502 while this information is filtered from each party by the UI server farm 102, which is protected behind a firewall 703 and various associated security measures discussed below. The market manager by also render other information for users 401 to indicate the market value of a certain information exchange, such as the price and terms of previous deals in which rights to relevant data was sold. In one embodiment, the market manager 505 makes a searchable database of previous transactions available for users 401 via the UI server 102. In one embodiment, when a transaction occurs, an electronic payment 506 is submitted by the buyer 501 to the system commercial interface 504 managed by the UI server farm 102, and a portion 507 is disbursed by the system interface 504 to the seller 502, a portion 509 to the market manager 505, a portion 508 to the validator 503 of the relevant information.

Distributed Users

Figure 6:
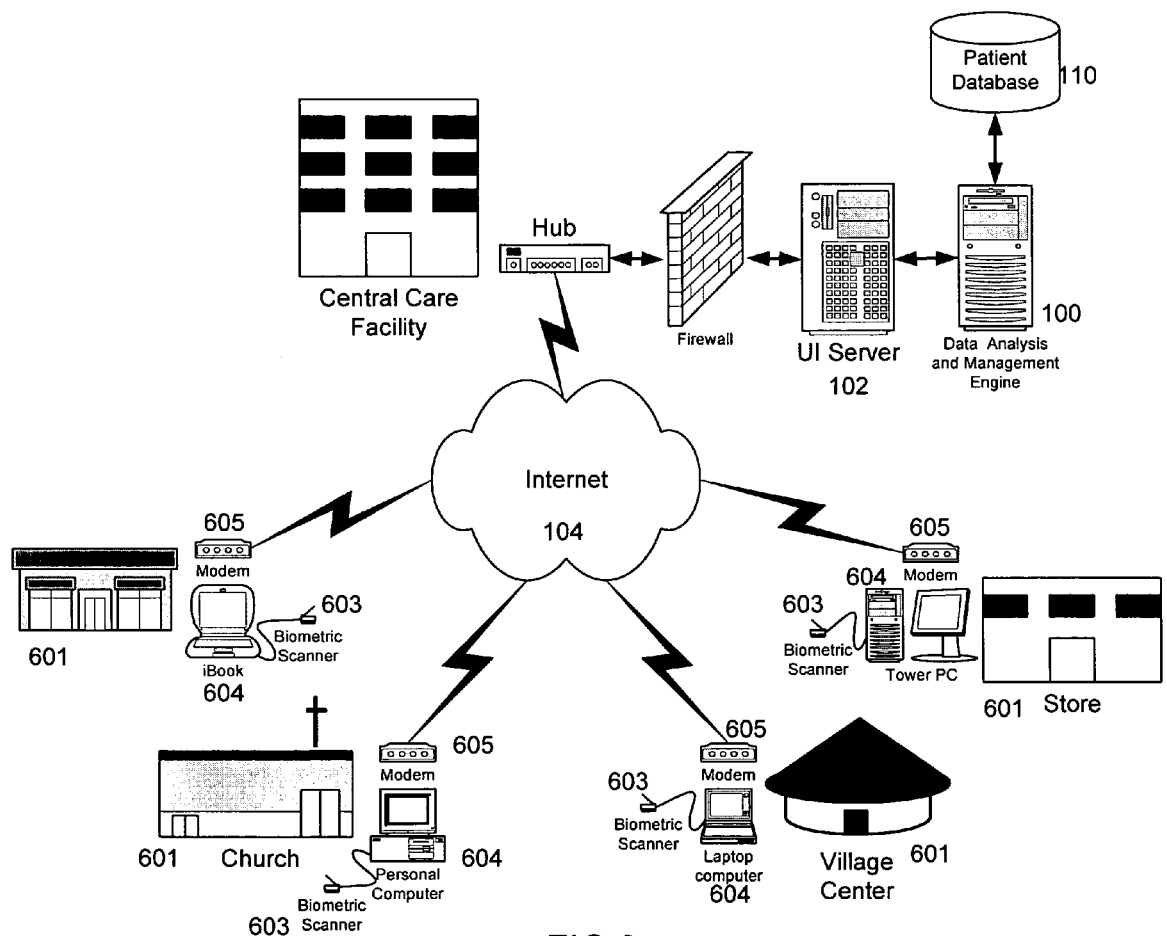
FIG. 6 illustrates one embodiment of the system in which distributed users access the system from remote locations using biometric authentication.

FIG. 6 illustrates one embodiment where the patient data 110 is accessed and updated by distributed users 401 via the UI server 102. In this particular embodiment, the users of the system are supervisors at Directly Observed Therapy DOT centers 601. The client terminals 604 all have a modem 605 that enables communication with the UI server 102 via the public internet 104. The UI server 102 enables access to the patient database 110 using a secure web interface (such as via https) with web-based messaging, and robust user authentication. In a preferred embodiment, each of the clients 604 has user authentication based on a biometric sensor 603, which can validate the identity of the supervisors to grant access to patient data 110. In one embodiment, the patient is also biometrically authenticated in order to automatically access their record when they arrive at a DOT site for treatment. The patient database 110 and the DAME 100 will restrict access by both function-level and data-level access privileges. Function-level access privilege, for example, will enable only caregivers to extract patient records from the database 110. Data-level access privilege, for example, will only allow the particular caregiver treating the relevant patient to extract their record from the database 110, or will not allow the caregiver access to patient contact information or any information beyond what is necessary to perform their work.

Data Security and Robust User Authentication

Figure 7:
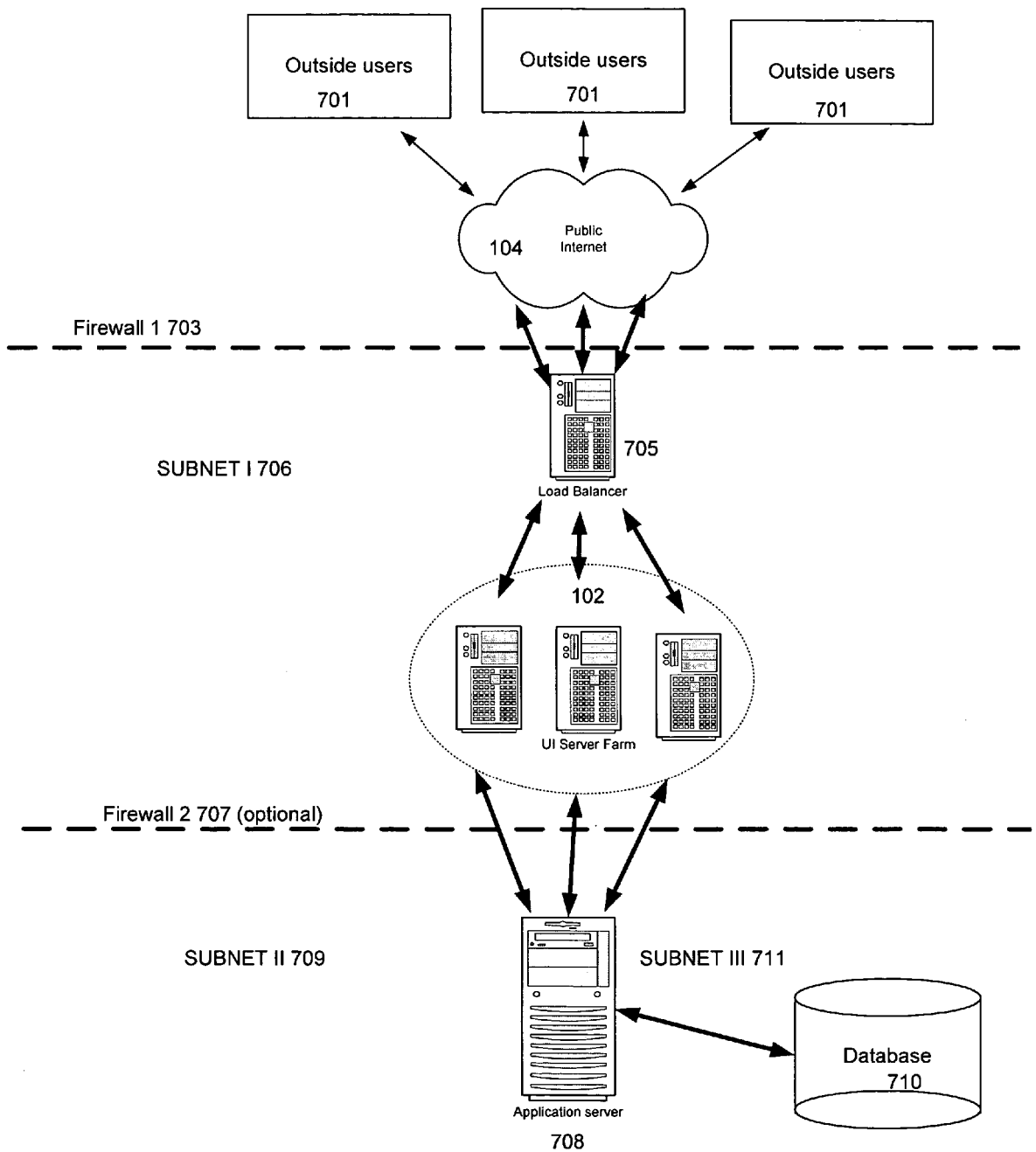
FIG. 7 describes one embodiment of the security architecture of the system.

The security architecture is illustrated in FIG. 1 and FIG. 7. In a preferred embodiment, the system will interact with users 401, namely caregivers 106, research organizations 107, or patients 105 by means of electronic messaging such as dynamic web-pages generated by the user interface servers 102 during a user's interaction with the system via the public internet 104. The system ensures the appropriate access to data for users by addressing security at multiple levels. In a preferred embodiment, user-level voluntary and involuntary password sharing is addressed by biometric authentication in addition to username/password access control. The biometric authentication device will be local to the user 401, and connected via the public internet 104 to the user authentication engine 101 at which the user 401 is authenticated. There exist several technology options to fulfill this need, including a variety of fingerprint and iris recognition devices. For purposes of identity confirmation, patterns on the human iris are more complex than fingerprints or facial patterns. The false-acceptance and false rejection rate for iris recognition is typically lower than that for fingerprint recognition. One compelling current alternatives is the Panasonic DT 120 Authenticam which is a small, web-enabled iris-scanning camera which can be connected to a PC by means of a USB port. The camera uses the Private ID Iris Recognition System software developed by Iridian, together with the Iridian Know Who Server operating on an ORACLE database. Another cost-effective device candidate is the Targus Defcon fingerprint scanner which van interface to a client device via Universal Serial Bus (USB).

In one embodiment of a high security architecture, all traffic from outside users 701 will be encrypted with 128 bits, and will be received through the internet (104) by a UI server 102 residing behind a the firewall #1 703. In the case of a UI server cluster, a load balancer 705 will be used to connect the user to the least loaded server in the farm. The firewall 703 will block all requests on all ports except those directly necessary to the system function. The function of the UI server is to encrypt/decrypt packages and to serve UI screens. In a preferred embodiment, the UI servers 102 do not store any data. Each UI server will have two NICs (network interface cards) and will exist simultaneously on two subnets, one accessible from the outside and one not. The application server 708 (that hosts the DAME) may be blocked from the UI server by another firewall 709, and will also exist on two subnets. Subnet I (706) is behind the firewall, but accessible from the outside. Subnet II (709) is between UI servers and application server (708), not accessible from the outside. In a preferred embodiment, the UI servers are separated from the application server by an additional Firewall II (707). In a preferred embodiment, application server(s) 708 still do not contain any data, but they are aware of the rules for data retrieval and manipulation. Like UI servers, application server(s) also have 2 NICs and exist on 2 subnets simultaneously: Subnet II (709) is between UI servers 102 and application server(s) 708, one password layer away from the outside, and behind a firewall. Subnet III (711) is between application server(s) and database (710), two password layers away from the outside, and behind one (optionally two) firewalls. Consequently, in the preferred embodiment, the database 710 is separated from the outside by two subnets and multiple firewalls.

In a preferred embodiment, the database 710 will be implemented using a robust industry-standard relational database platform from a vendor such as ORACLE and a UNIX-family operating system. In a preferred embodiment, access to each server is logged, and repetitive unsuccessful logins and unusual activities (possible attacks) are reported. Should local client data be stored, it will be encrypted (128 bits). Decryption keys are supplied by the server on logins and updated in regular intervals when client connects to the server (in case of offline work), or real time (in case of online work).

Operating Systems, Web Servers, Database and Programming Languages

In a preferred embodiment: The server operating system of choice is 64 bit LINUX. The database is based on ORACLE, insofar as it is both the industry leader for databases and an emerging leader in the life sciences industry and is fully interoperable with the LINUX operating system. System web servers run Apache, with PHP used to retrieve and construct dynamic content. This tool allows web page content to be published without the need for complex coding. An Extract-Transform-Load (ETL) tool is used to move data into the permanent database. The software languages are a combination of JAVA, PL/SQL language and C/C++. These languages are all widely adopted within the software industry and allow maximum flexibility to coders. Data Warehousing/presentation tools will be supplied by Oracle. The front end application servers will be implemented in Java.

Example of the Data Taxonomy

In a preferred embodiment, patient data will span these four categories

1. Patient profile information (112), standardized as per (118): Demographic and administrative information.
2. Patient Diagnostic Information (116), standardized as per (119): Clinical assessment information and laboratory tests including genetic information.
3. Patient Symptomatic Information (113), standardized as per (117): Clinical information based on physical presentation of patient, and laboratory phenotype tests.
4. Patient Treatment Information (115), standardized as per (121): Clinical interventions such as medications.

In order to make this explanation concrete, the following example describes the information that may be contained in the standardized patient database, specifically pertaining to patients with AIDS and who have been or will be subjected to anti-retroviral therapy. Not all the information described here will typically be available. In addition, this describes both the type of information that would be in the standardized data model (profile information 112, symptomatic information 113, treatment information 114, diagnostic information 115), as well as the type of information that would go into supporting tables (such as the drug dispense table and the lab test table). For illustrative purposes, the data classes related to patient diagnostic and treatment information have been labeled in brackets with a data class definition according to the UMLS Metathesaurus.

Figure 8:
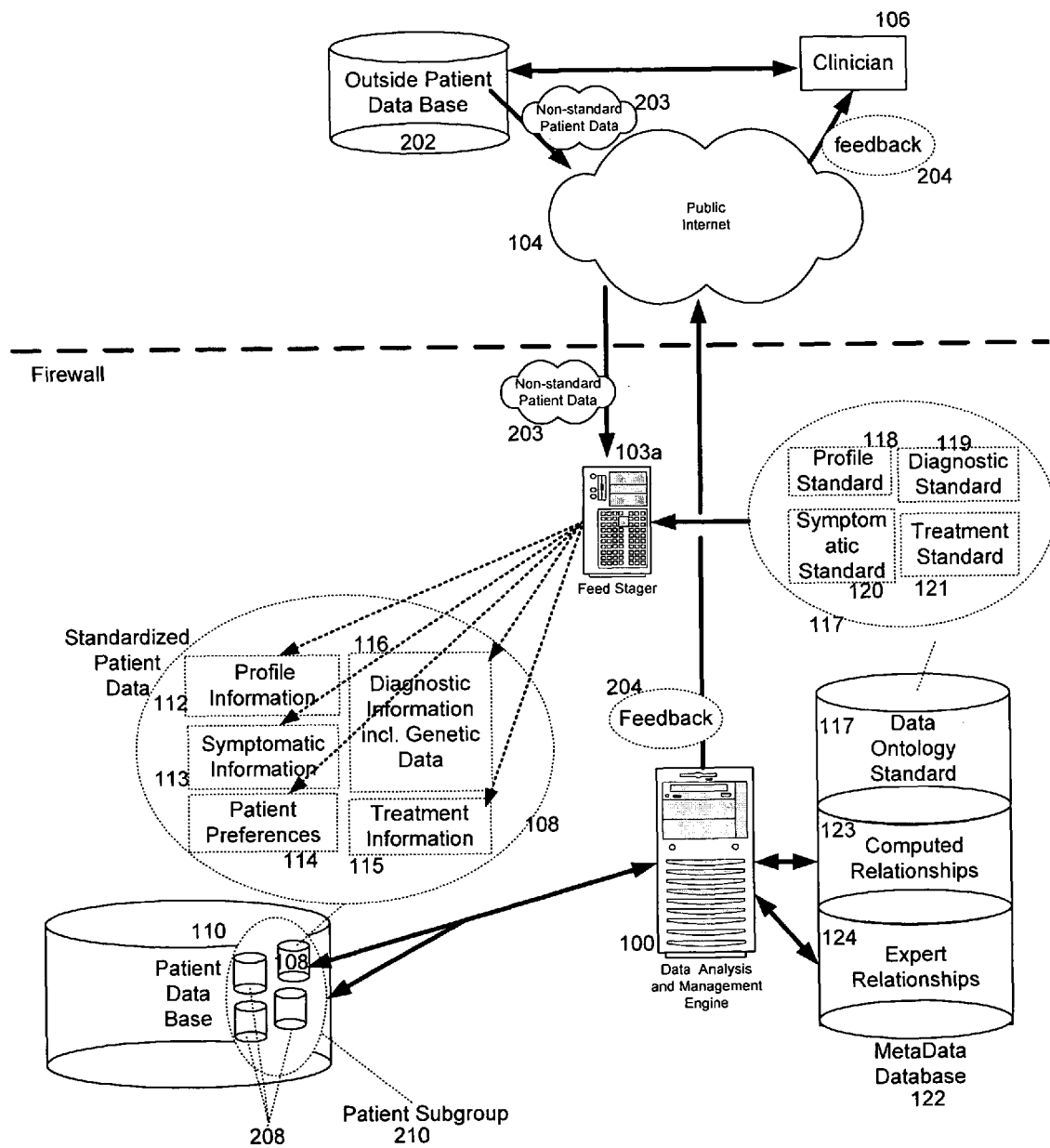
FIG. 8 describes one embodiment of how the system supports decisions by caregivers based on electronic data from a particular patient compared against electronic data from other patients.

1. Patient Profile (Indexed by Patient ID)
   a. Patient ID (the only aspect of profile almost always available; usually a scrambled identifier to be HIPAA compliant)
   b. Name
   c. SSN
   d. Age
   e. Gender
   f. Race
   g. Mailing Address
   h. Work Telephone Number
   i. Home Telephone Number
   j. E-mail
   k. Others
2. Patient Diagnostic Information (Indexed by Patient ID)
   a. Patient ID (UMLS: C0600091)
   b. Set of Gene Tests (C0679560), for each
      i. Lab Test ID (C1317858)
      ii. Validator ID (C0401842)
      iii. Date (C0011008)
      iv. Subtype
         1. HIV1 (C0019704)
         2. HIV2 (C0019707)
         3. NHPL
      v. RT (Encoding Reverse Transcriptase Enzyme) (C0121925)
         1. Raw Nucleotide Sequence in FASTA format
         2. Aligned Nucleotide Sequence in FASTA format
         3. Raw Amino Acid Sequence in FASTA format
         4. Aligned Amino Acid Sequence in FASTA format
         5. List of all mutations from wild-type in the form D67N, K70R . . . (i.e. wild-type amino acid, location, mutant amino acid)
      vi. PR (Encoding Protease Enzyme) (C0917721) <same format as RT>
      vii. Sections of the GAG (Group Specific Antigen) gene such as proteins p24, p7, p15, p55 (C0062792, C0062793, C0062797, C0062799, C0082905, C0121919, C0168493, C0219721, C0662000, C0669519) <same format as RT>
      viii. Sections of the POL gene such as proteins p10, p51, p66, p31 (C0294131, C0637975, C1098512) <same format as RT>
      ix. Sections of the ENV gene such as glycoproteins gp41 and gp120. (C0019691, C0019692, C0062786, C0062790, C0062791, C0659096) <same format as RT>
   c. Others (including human genes in addition to viral genes)
3. Patient Symptomatic Information (Indexed by Patient ID)
   a. Patient ID
   b. Set of CD4+ Counts, for each
      i. Lab Test ID
      ii. Validator ID
      iii. Date
      iv. Count
      v. Unit
      vi. Other
   c. Set of Viral Load Counts, for each
      i. Lab Test ID
      ii. Validator ID
      iii. Date
      iv. Count
      v. Unit
      vi. Other
   d. Set of In-vitro Phenotypic Test
      i. Lab Test ID
      ii. Validator ID
      iii. Date
      iv. <Susceptibility to each drug tested—various formats>
      v. Other
   e. Other (including possibly clinical symptoms such as body mass etc.)
4. Patient Treatment Information (Indexed by Patient ID)
   a. Patient ID (C0600091)
   b. Set of drugs received, for each
      i. Dispense ID
      ii. Date (C0011008)
      iii. Validator ID (Data Process Manager, C0401842)
      iv. Drug Specification
         1. NRTI (Nucleoside Reverse Transcriptase Inhibitors) (C01373111)
            a. d4T (C0164662)
            b. 3TC (C0209738)
            c. AZT/3TC (C0667846)
            d. ddI (C0012133)
            e. ABC (C0724476)
            f. TFN (C11101609)
            g. ZDV/3TC/ABC (C0939514)
            h. ZDV (C0043474)
            i. ddC (C0012132)
         2. NNRTI (Non-Nucleoside Reverse Transcriptase Inhibitors) (C1373120)
            a. EFV (C0674427)
            b. NVP (C0728726)
            c. DLV (C0288165)
         3. PI (Protease Inhibitors) (C0033607)
            a. NFV (C0525005)
            b. LPV/r (C0939357)
            c. IDV (C0376637)
            d. RTV (C0292818)
            e. SQV (C0286738)
            f. APV (C0754188)
            g. ATV (C1145759)
      v. Measures of patient adherence measures
   c. Others
5. Drug Dispense Tables (Indexed by Dispense ID)
   a. Dispense date
   b. Dispensed drug name
   c. Quantity dispensed
   d. Days supply
   e. Refills number
   f. Directions
   g. Clinic ID
   h. Physician ID
   i. Other 6. Lab Test Tables (Indexed by Lab Test ID)
   a. Lab Test ID
   b. Test Date
   c. Validator ID
   d. Order Station ID
   e. Test Station ID
   f. Report Date
   g. Type: One of (Gene Sequence, Blood Count, Phenotypic Test, Other)
      i. Gene Sequence
         1. Method ID
         2. Subtype
            a. one of (HIV1, HIV2, NHPL)
            b. one of (MAIN, CPZs, O)
            c. one of (B, non B, A, C, D, F, G, H, J, K, CRF01_AE, CRF02_AG)
         3. RT (Encoding Reverse Transcriptase Enzyme)
            a. Raw Nucleotide Sequence in FASTA format
            b. Aligned Nucleotide Sequence in FASTA format
            c. Raw Amino Acid Sequence in FASTA format
            d. Aligned Amino Acid Sequence in FASTA format
            e. List of all mutations from wild-type in the form D67N, K70R ... (i.e. wild-type amino acid, location, mutant amino acid)
         4. PR (Encoding Protease Enzyme) <same format as RT>
         5. Sections of the GAG (Group Specific Antigen Gene) such as proteins p24, p7, p15, p55 <same format as RT>
         6. Sections of the POL gene such as proteins p10, p51, p66, p31 <same format as RT>
         7. Sections of the ENV gene such as glycoproteins gp41 and gp120. <same format as RT>
         8. Other
      ii. In-vitro Phenotypic Test
         1. Method ID
         2. <Susceptibility to each drug tested—various formats>
         3. Other
      iii. Blood Counts
         1. CD4+ Count
            a. Method ID
            b. Count
            c. Unit
            d. Other
         2. Viral Load Count
            a. Method ID
            b. Count
            c. Unit
            d. Other
      iv. Other The Use of the Invention to Help Clinicians Make Decisions FIG. 8 describes the process by which clinical feedback can be provided, and predictions can be made using the Data Analysis and Management Engine (DAME) 100 and the Meta-Data database 122. This figure only describes one embodiment of the invention for illustrative purposes and should not be interpreted to constrain the way in which information flows according to the invention. A clinician 106 will select from a local patient database 202 data for a particular patient 203 that need not be structured according to the standardized templates 117. This data is uploaded via the internet 104 or some other communication channel to the feed stager 103a, and as described above, it is then parsed and validated (via the feed parser 103b, feed validator 407, and DAME 100) into standardized patient data 108 that is formatted according to the data model standard 117. The DAME 100 can then apply the set of computed statistical relationships 123 and expert relationships 124 to provide feedback 204 to the clinician based on the data 108 such as, for example, a predicted clinical outcome as described below. In this way, the combination of computed statistical relationships 123, expert relationships 124, and the data model standard 117 can generate useful feedback for a particular patient's data 203. It will be clear to one skilled in the art after reading this disclosure how the system can be used to make recommendations for treatment, rather than predict outcomes in response to treatments proposed by the clinician 106. This would involve cycling through a range of different possible treatments based on the expert relationships 124 and comparing the predicted outcome for each. In addition, the DAME 100 will aggregate the new patient data 108 with data of existing patients 208 in the relevant patient subgroup 210 in order to generate up-to-date computed statistical relationships 123 to be applied to other predictive problems. The following section discusses methods that can be applied to generating feedback 204 for the clinician 106 and generating the computed statistical relationships 123 in the standardized data model database by the DAME 100. A user interface for a clinician is then described according to a one embodiment.

Known Methods for Computing Statistical Relationships in the Standardized Data Model Database 122 and for Making Predictions 204

This section describes statistical methods that can be applied in the DAME 100 to generate the computed statistical relationships 123 between the standardized data classes 117 that are contained in the standardized data model database 122, and that can be applied to generating feedback 204 about a particular subject. An exhaustive list is not provided, rather a limited subset of methods is provided to illustrate the concept of how the computed statistical relationships can be generated using the relevant set of subject data and used in the standardized data model database 122.

Determining the Validity of Data for a Patient 108 in a Subgroup 210:

It has been described how the DAME 100 can use a regression model of one or multiple variables to model some data class, or random variable for all patients in a subgroup 210, so that it is known when data 112-116 is sufficiently unlikely that it should be flagged as erroneous. It was assumed for simplicity that the distribution of the variable is approximately Gaussian; however a similar approach applies to variables with other probability distributions such as categorical variables. More details of one embodiment of the approach is now described, starting with modeling the probability distribution of a single random variable $X_{f,n}$. Assume that the true mean of the variable $X_{f,n}$ is $\mu_f$. The DAME estimates $\mu_f$ with the sample mean $$\overline{X_f} = \frac{1}{N} \sum_{n=1}^{N} X_{f,n} \tag{1}$$

The DAME computes the sample variance of $X_{f,n}$ over the set of N patients in the subgroup 210

$$V_f^2 = \frac{1}{N-1} \sum_{i=1}^{N} \left( X_{f,i} - \frac{1}{N} \sum_{n=1}^{N} X_{f,n} \right)^2 \tag{2}$$

Given the DAME's estimate of mean and variance of the subgroup 210, assume that it next considers the data class $X_{f,N+1}$ associated with a new patient data 108, and finds that it has some value $x_{f,N+1}$ which is greater than the sample mean. DAME can estimate the probability of this value, given the assumptions that patient N+1 belongs in the same subgroup 210 as the other N patients 208. Namely, assuming that $X_{f,N+1}$ is a normally distributed random variable, and given the measurements of sample mean $\overline{X}_f$ and sample variance $V_f$ based on the previous N samples, the DAME can determine the probability $PR\{X_{f,N+1} >= x_{f,N+1}\}$. If the DAME 100 finds this probability to be very small (below some threshold) then it questions whether $X_{f,N+1}$ is valid and whether patient N+1 belongs in the same subgroup 210 as the previous N patients. Let the estimated variance of $X_{f,N+1}$ be $s(X_{f,N+1} - \overline{X}_f)$ and break down the value $x_{f,N+1}$:

$$x_{f,N+1} = \overline{X}_f + t_f s(X_{f,N+1} - \overline{X}_f) \quad (3)$$

where $t_f$ is some multiplier of the sample variance that determines the extent of the distance from the sample mean to the value $x_{f,N+1}$. It can be shown that the probability $Pr\{X_{f,N+1} >= x_{f,N+1}\}$ can be rewritten as:

$$Pr\left\{\frac{X_{f,N+1} - \overline{X}_f}{\sqrt{V_f^2\left(1 + \frac{1}{N}\right)}} >= t_f\right\} = Pr\left\{\frac{\frac{X_{f,N+1} - \overline{X}_f}{\sigma_f \sqrt{1 + \frac{1}{N}}}}{\sqrt{\frac{V_f^2(N-1)}{\sigma_f^2} \cdot \frac{1}{N-1}}} >= t_f\right\} \quad (4)$$

Now, $(X_{f,N+1} - \overline{X}_f)/(\sigma_f \sqrt{1+1/N})$ is a normally distributed random variable with unit variance and zero mean, and it can be shown that $V_f^2(N-1)/\sigma_f^2$ is a chi-squared random variable with N−1 degrees of freedom. Therefore, the left hand side of the inequality has a chi-squared distribution with N−1 degress of freedom, and can be set equal to random variable $T_{N-1}$ which has a Student-T distribution with N−1 degrees of freedom $f_{T,N-1}(t)$. So the probability $Pr\{X_{f,N+1} >= x_{f,N+1}\}$ can be computed as $$Pr\{T_{N-1} >= t_f\} = \int_{t_f}^{\infty} f_{T,N-1}(t)dt = F_{T,N-1}(t_f) \quad (5)$$

A value for $t_f$ is picked such the cumulative Student-T distribution function with N−1 degrees of freedom, $F_{T,N-1}(t_f)$, is equal to some probability bound, $\alpha/2$. This value of $t_f$ is denoted as $t(\alpha/2, N-1)$—this notation will be used in a later section. Then, assuming that the data is valid, there is a probability of $1-\alpha/2$ that $T_{N-1} < t_f$. So far, only the upper bound on $X_{f,n}$ has been considered; the lower bound is dealt with just the same way. Considering the upper and lower bound, there is a probability of $\alpha$ that $|T_{N-1}| >= t_f$. If $\alpha$ is (based on the expected reliability of the data) sufficiently small, but the DAME finds that $|T_{N-1}| >= t_f$, then the DAME 100 will flag the new patient data as potentially containing a bad data class $X_{f,n+1}$ or being in the wrong subgroup 210.

Figure 9:
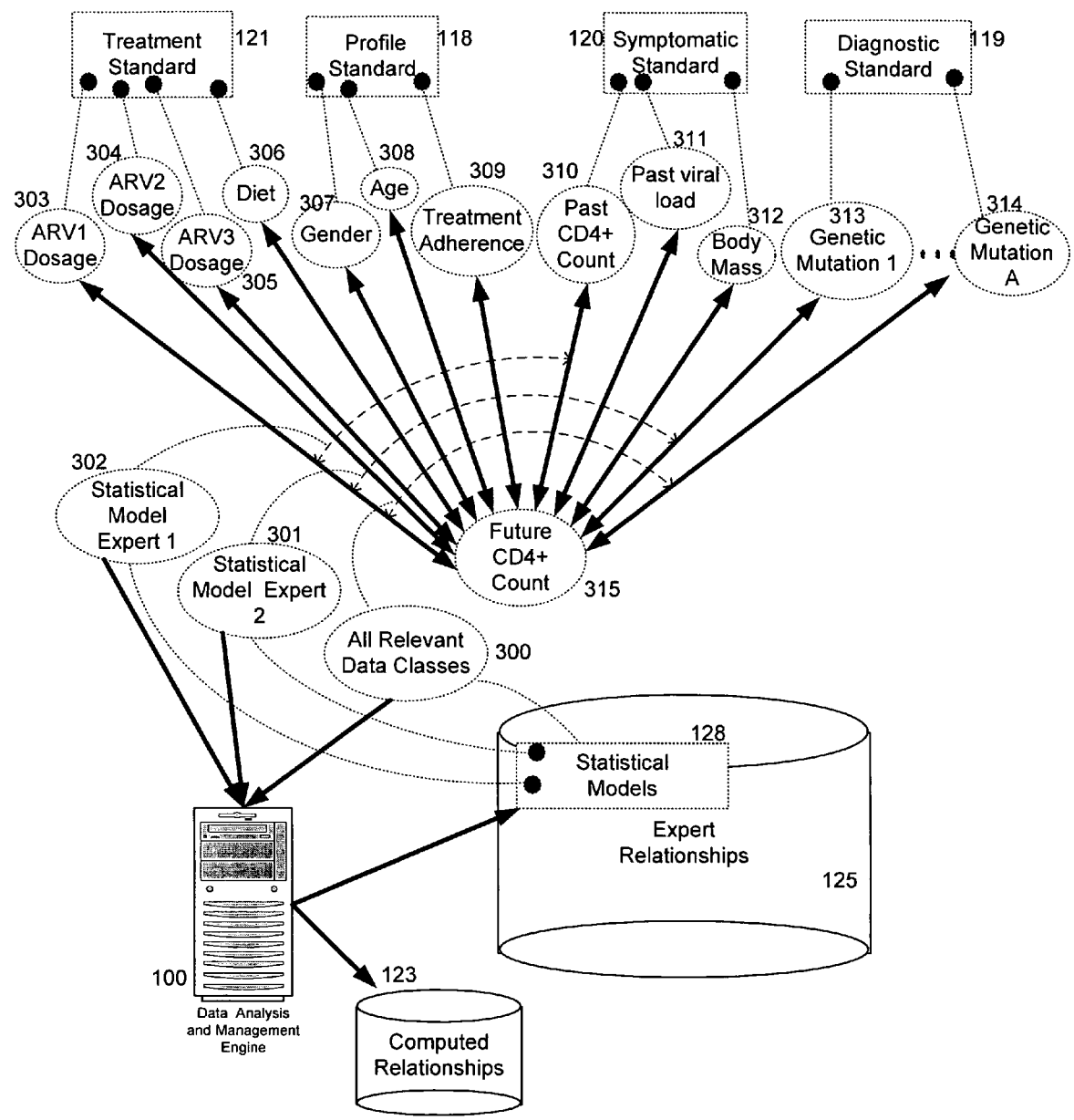
FIG. 9 describes one embodiment for how the system uses multiple different expert statistical models in order to make predictions of clinical outcome based on inhaled patient data.

The Use of Expert Relationships 125 and Computed Statistical Relationships 123 FIG. 9 illustrates the synergy between expert relationships 125 and computed relationships 123 in one embodiment of the invention. This is illustrated with reference to a particular example, where the data class of interest is future CD4+ cell count of a patient with Human Immunodeficiency Virus HIV. This data class is divided in the figure into two subclasses namely past CD4+ count 310 and future CD4+ count 315. In this example, the DAME 100 makes a prediction on the future value of CD4+ count based on a series of relevant data classes from the data model standards 118-121, combined with expert relationships 124 and computed relationships 123 stored in the meta-data databases 122.

The DAME 100 uses the algorithmic relationships from experts 301, 302 in order to determine which variables are relevant to modeling future CD 4 count 115, and in what way these relevant variables should be included in the model. In one embodiment, the algorithmic relationships 301,302 from various experts are electronically published according to a standard template and downloaded for conversion by the feed parser 103b into a form that it can be stored in the expert relationships database 124 and applied to the data model standard 117. In order for an expert to specify a statistical model, the expert publishes the standardized data classes, or independent variables, used by the model; a training function that trains the parameters for the model; and a mapping function that inputs the relevant standardized data classes and the trained parameters in order to predict the datum of interest. For example, each hypothesis validated in a clinical trial may be electronically published in this way. In one embodiment, the expert also publishes as set of raw patient data that is either formatted according to the standardized data classes, or is accompanied by a translation cartridge, so that the data can be automatically inhaled into the standardized ontology, and can be acted upon by the published training and mapping functions in order to replicate the results published by the expert, and to refine these results as more data is inhaled. The algorithmic relationships 301,302 illustrated in FIG. 9 specify the set of data classes that different experts used to predict the relevant outcome 315, as well as a training function and mapping function describing how those data classes were mathematically manipulated in order to model the relevant outcome 315. The item "all relevant data classes" 300 represents the union of all of the relevant data classes used as independent variables by different statistical models in the algorithmic relationships database 128 that relate to the relevant outcome 315. In this illustrative example, expert 1 includes nine variables 303-311 in the model for future CD4+ count 315, but does not include body mass data class 312 or mutations 1 313 to mutations A 314 data classes, which may represent human or viral mutations, as relevant independent variables in the model. Expert 2 does include body mass and mutation 1 314 in the model, but not include the data classes relating to the other mutations up to mutation A 314. In one embodiment, the model is a regression analysis model. In this case, the DAME 100 is guided by the algorithmic relationships 301, 302 in terms of what independent variables to select for regression analysis, and what mathematical operations to perform on those variables in order to include them in the regression model so that it may compute regression parameters for the computed relationships database 124. The DAME 100 may then select a particular model, or select a particular subset of independent variables in a model, in order to make the best prediction.

Application of Regression Analysis to Generating Computed Relationships 123 and Feedback 204:

In order to illustrate the use of regression analysis according to one embodiment, assume that a clinician is addressing the problem of what mixture of Anti-Retroviral Drugs (ARV) should be given to a patient at a particular stage of progression of an HIV/AIDS infection and immune system degradation.

In order to illustrate the statistical approach, three separate questions are considered that can be addressed by the DAME 100. These example questions are merely illustrative and by no means exhaustive:

1. How can the DAME make predictions 204 using data in the standardized data model database 122, and how can it establish when a patient's data 108 appears to be inconsistent with their diagnosis and/or treatment?
2. How can the DAME use statistical analysis to determine the level of precision in the computed relationships 123 that the patient data base 110 will be able to support? e.g. If people with different stages of disease progression respond differently to the ARV regimens, so that the DAME should prescribe different ARV regimens for different stages of disease progression, how narrowly should the DAME define the subgroups of people with particular stages of disease progression, in order to prescribe a set of ARV's that is well supported by the available patient data base 110?
3. How can the DAME use statistical tools to understand the ideal doses that should be administered to a patient?

For simplicity, assume only the ARV drug dosages are considered as relevant independent variables for modeling the progression of the disease. Assume that the progress of the HIV/AIDS virus is tracked by monitoring $\vec{X}_{TLC,n,t}$, the measure of the Total Lymphocite Count, over time. It has recently been shown that TLC count and Hemoglobin levels are an effective measure of the progress of the HIV/AIDS infection, and can be used instead of the more expensive CD4+ cell counts. Of course, nothing in this example would change if use was made of the more conventional CD4+ count to track disease progress. The set of data classes relevant to our hypothetical example are:

$\vec{X}_{TLC,n,t}$ represents the set, or vector, of TLC Counts for patient n over the some time interval up to time t. Assume that the patient n is specified by some kind of unique patient identifier. If patient n has been monitored each month for $t_n$ months, represent the set of the patient's TLC counts $\vec{X}_{TLC,n,t}=[X_{TLC,n,t-t_n} \ldots X_{TLC,n,t-1}, X_{TLC,n,t}]$ $\vec{X}_{ARV1,n,t}$ represents the dosage of ARV1 for patient n, sampled for each month leading up to the time t. $\vec{X}_{ARV1,n,t}=[X_{ARV1,n,t-t_n} \ldots X_{ARV1,n,t-1} X_{ARV1,n,t}]$ $\vec{X}_{ARV2,n,t}$ represents the dosage of ARV2 for patient n, sampled for each month leading up to the time t.

$\vec{X}_{ARV3,n,t}$ represents the dosage of ARV3 for patient n, sampled for each month leading up to the time t.

One can monitor how data class $\vec{X}_{TLC,n,t}$ varies with respect to the data classes $\vec{X}_{ARV1,n,t}, \vec{X}_{ARV2,n,t}$ and $\vec{X}_{ARV3,n,t}$ by establishing a regression model:

$$f_{TLC}(\vec{X}_{TLC,n,t}) = \sum_{p=0}^{P-1} \beta_p f_p(\vec{X}_{ARV1,n,t}, \vec{X}_{ARV2,n,t}, \vec{X}_{ARV3,n,t}) + \varepsilon_n$$

where the dependent variable is some function of data class $\vec{X}_{TLC,n,t}$, and the independent variables are functions of data classes $\vec{X}_{ARV1,n,t}, \vec{X}_{ARV2,n,t}$ and $\vec{X}_{ARV3,n,t}$. The regression parameters to be estimated are $\beta_0 \ldots \beta_{P-1}$ and the modeling error is characterized by $\varepsilon_n$. The equation above is a very generic formulation of the relationship between the data classes which is suitable for regression analysis. Based on the particular question at hand, it will be clear to one skilled in the art, after reading this disclosure, how to specify the functions $f_{TLC}$ and $f_p$. In our example, assume the function $f_{TLC}$ measures the change in the log of the TLC count over a period of $t_\alpha$ months of receiving the regimen of ARVs. For simplicity, notate the dependent variable in the regression as $Y_n$ and describe this as follows:

$$Y_n = f_{TLC}(\vec{X}_{n,t,TLC}) = \log(X_{TLC,n,t}) - \log(X_{TLC,n,t-t_\alpha}) \quad (6)$$

Of course, many different functions $f_{TLC}$ are possible. Often, in designing the function for generating the dependent variable, the goal is to make the resultant variable as linear in the independent variables as possible. Equation (6) assumes that the use of the logarithm would be effective. However, this is purely illustrative and is not necessarily an optimal approach. Let functions $f_0 \ldots f_{P-1}$ be linear in the data $\vec{X}_{ARV1,n,t}, \vec{X}_{ARV2,n,t}$ and $\vec{X}_{ARV3,n,t}$, and represent the average dosage of each of the ARTs for the period of $t_\alpha$ months leading up to t. Assume for the example that the number of parameters P=4 and simplify the above Equation as follows:

$$f_{TLC}(\vec{X}_{n,t,TLC}) = \beta_0 + \sum_{p=1}^{P-1} \beta_p f_p(\vec{X}_{ARVp,n,t}) + \varepsilon_n \quad (7)$$

where $$f_p(\vec{X}_{ARVp,n,t}) = \frac{1}{t_\alpha} \sum_{k=t-t_\alpha}^{t} X_{ARVp,n,k} \quad (8)$$

Define the new independent regression variables $X_{p,n}=f_p(\vec{X}_{ARVp,n,k})$ for $p \neq 0$ and $X_{0,n}=1$ and so that the fundamental regression Equation is rewritten $$Y_n = \sum_{p=0}^{P-1} \beta_p X_{p,n} + \varepsilon_n, \quad n = 1 \ldots N \quad (9)$$

Represent these equations for N patients in the form of a matrix equation $$Y = Xb + \epsilon \quad (10)$$

Where $$Y = \begin{bmatrix} Y_0 \\ \vdots \\ Y_{N-1} \end{bmatrix}, X = \begin{bmatrix} 1 & X_{1,0} & \cdots & X_{P-1,0} \\ \vdots & \vdots & & \vdots \\ 1 & X_{1,N-1} & \cdots & X_{P-1,N-1} \end{bmatrix}, \quad (11)$$

$$b = \begin{bmatrix} b_0 \\ \vdots \\ b_{N-1} \end{bmatrix}, \varepsilon = \begin{bmatrix} \varepsilon_0 \\ \vdots \\ \varepsilon_{N-1} \end{bmatrix}$$

Assuming that the disturbance is normally distributed, $\epsilon \sim N(0, I\sigma^2)$, the least-squares, and maximum-likelihood, solution to Equation (15) is given by:

$$b = (X^T X)^{-1} X^T Y \quad (12)$$

It should be noted that if (as in the more general case) the disturbances are correlated and have covariance C and non-zero mean $\mu$, so that $\epsilon \sim N(\mu, C)$, then the least-squares solution is $b = (X^T C^{-1} X)^{-1} X^T C^{-1}(Y - \eta)$. Based on the regression model, for some new patient N, and a proposed ART dosage $X_N$, one can predict what the expected change in the patients TLC count will be:

$$\hat{Y}_N = X_N b \tag{13}$$

Using the Confidence Bounds for Multivariate Regression:

One also seeks to determine the confidence bounds for the prediction so that one can, for example, judge when a particular patient is not responding as expected to a particular treatment regimen or when their data is not internally consistent. As discussed above, the $1-\alpha$ confidence bound for $Y_N$ is given by:

$$\hat{Y}_N \pm t\left(1 - \frac{\alpha}{2}, N - P\right) s(\hat{Y}_N - Y_N) \tag{14}$$

where $$t\left(1 - \frac{\alpha}{2}, N - P\right)$$

is chosen such that the cumulative Student-T distribution with $N-P$ degrees of freedom is equal to $\alpha/2$ at that value i.e. $F_{T,N-P}(t(1-\alpha/2, N-p))=\alpha/2$; and where $s(\hat{Y}_N-Y_N)$ is an unbiased estimate of the covariance $\sigma(\hat{Y}_N-Y_N)$ based on the data. It can be shown that $$\sigma^2(\hat{Y}_N - Y_N) = \sigma^2(\hat{Y}_N) + \sigma^2(Y_N) = \sigma^2 X_N^T (X^T X)^{-1} X_N + \sigma^2 \tag{15}$$

Since the actual value of $\sigma^2$ is not know, use the unbiased estimator termed the Mean-Squared-Error (MSE) which measures the Sum of the Squared Error (SSE) of the estimate, per degree of freedom. The SSE, as defined, is computed from:

$$SSE = (Y - \hat{Y})^T (Y - \hat{Y}) \tag{16}$$

where $\hat{Y} = Xb$. There are N measurements with uncorrelated disturbances, or N "degrees of freedom", which go into generating Y. Since one must estimate P parameters in order to create the estimate $\hat{Y}$, one gives up P degrees of freedom in SSE, so the total degrees of freedom in SSE is $N-P$. Hence one computes $$MSE = \frac{SSE}{N - P} \tag{17}$$

It can be shown that the expectation value $E\{MSE\}=\sigma^2$. Consequently, $$s^2(\hat{Y}_N - Y_N) = MSE(X_N^T (X^T X)^{-1} X_N + 1) \tag{18}$$

Hence, if patient N has a decrease in TLC count which places the patient's data out of the range of $$\hat{Y}_N \pm t\left(1 - \frac{\alpha}{2}, N - P\right) s(\hat{Y}_N - Y_N),$$

it may be concluded that there is only a likelihood $\alpha$ of this happening by statistical anomaly if all assumptions are correct, and the patient's record is flagged for re-examination of the assumptions.

Consideration for Dividing Patients into Groups in Statistical Models 128:

Regarding the second question, how does one determine the level of specificity with which to subdivide patients into groups to determine regression parameters (or other statistical properties) of a particular group. A simple way of addressing this issue, in a preferred embodiment, is to seek the lower bound that it places on the number of patients that are necessary as data points in order for the results of the analysis to be statistically significant. For example, consider the situation described above, except add the complication that the response of patients to different ARV regimens varies significantly based on the stage of degradation of the patient's immune system. In this case, rather than create a single linear model as described in Equation (15), create a piecewise linear model. The relevant group is determined by the patient's TLC count when ARV treatment is initiated at time $t-t_\alpha$. The model can then be characterized:

$$Y = \begin{cases} X_0 b_0 + \varepsilon_0 & \text{for } x_0 \leq X_{n,t-l,TLC} < x_1 \\ X_1 b_1 + \varepsilon_1 & \text{for } x_1 \leq X_{n,t-l,TLC} < x_2 \\ \vdots & \vdots \\ X_{D-1} b_{D-1} + \varepsilon_{D-1} & \text{for } x_{D-1} \leq X_{n,t-l,TLC} < x_D \end{cases} \tag{19}$$

Rather than determine a single set of parameters, b, determine D sets of parameters, each for a different domain of TLC count, or a different domain of disease progression. The data can be divided into domains, D, based on the amount of patient data that is available in order to determine the parameters relevant to each domain in a statistically significant manner. Divide up the total set of N patients into each of the relevant domains such that $$N = \sum_{i=0}^{D-1} N_d.$$

Consider domain d, to which is assigned the parameters $b_d$ and the number of patients $N_d$. The variance of the parameters for that domain can be estimated based on the $N_d$ patient records that fit into that domain, using the same technique described above. Assume that the variance on the resultant parameter estimates is $\sigma^2(b_d)$. It can be shown that the unbiased estimator for the variance is:

$$S^2(b_d) = MSE(X_d^T X_d)^{-1} \tag{20}$$

Where MSE is calculated as described above. From the diagonal elements of the matrix $s^2(b_d)$, one can obtain the variance of individual elements of the parameter matrix, namely $s^2(b_{d,p})$, where that is the variance of parameters in the vector $b_d$, which is an estimate of $\beta_{d,p}$. For the normal regression model, and using similar arguments to those described above, it can be shown that the $1-\alpha$ confidence limit for our estimate of $\beta_{d,p}$ is given by:

$$b_{d,p} \pm t(1-\alpha/2; N_d-P) s(b_{d,p}) \tag{21}$$

Assume a choice of $\alpha=0.05$ so that one finds the 90% confidence interval. One may now compare the parameters calculated for domain d with those parameters calculated for domains d−1 and d+1. In one embodiment, one wishes to establish that the differences between the parameters in adjacent domains are greater than the confidence interval for the estimates of parameters in the domains. For example, in a preferred embodiment, one seeks to ensure that $$|b_{d,p} - b_{d-1,p}|, |b_{d,p} - b_{d+1,p}| > t(1-\alpha/2; N_d-P) s(b_{d,p}) \tag{22}$$

Note that the setting of α is the choice of the user of system, and determines the level of confidence that is sought in the bounds that are defined for the regression parameters. If the above inequalities are not satisfied, then the solution may be to increasing the size of each group so that the resulting parameters for each group are clearly differentiated in a statistically significant way.

Recommending Preferred Treatment Methodologies Using Computed Relationships 123 Based on Statistical Models 128:

The third question is new addressed, namely how one uses these tools that perform statistical analysis between data classes to recommend preferred methodologies for treatment. Applying the technique described above, the response of a subject can be modeled in terms of the expected change in their TLC count over some time period $t_\alpha$ during which they are subjected to a particular regimen of ARV's. This response is based on the data of previous subjects whose data contains the relevant independent variables—in this case, ART dosage—and for whom the relevant outcome has been measured—in this case TLC count. By breaking down subjects into smaller groups, one creates an accurate model for Y, based on $X_d$, where d is the domain or group into which the subject fits. In each domain d, based on the parameters $b_d$ that are estimated, One has an unbiased estimate of the change expected in TLC count with respect to a particular drug, p:

$$\frac{\partial \hat{Y}}{\partial X_{d,p}} = b_{d,p} \quad (23)$$

In the context of ARV medication, because the system is not linear, one could not say that because $b_{d,p}$ is positive, one will increase the expected value of $\hat{Y}$ indefinitely as one increases the dosage of ARV p. One approach, in a preferred embodiment, is that data class ARV p already has a expert-based rule associated with it, namely that this ARV p should not be given in doses exceeding a certain quantity either because it causes side effects or because the dosage reaches a point of diminishing returns. Consequently, if $b_{d,p}$ is large and positive, the DAME 100 will prescribe a dosage of ARV p that is the limit defined by the expert-based rules.

Another approach to determining the best drug regimen would involve selecting those patients showing the largest change in Y, and modeling the parameters b for that set of highly successful cases. Initially, one doesn't know what combination of ARVs will perform best. Assume one has $\tilde{P}$ different drugs to choose from, and that the number of drugs that a patient can be administered is P. The initial process would involve cycling through each of the $\tilde{P}$ drugs for a range of patients, each of whom only receives a set of P drugs, until one can determine with a reasonable degree of certainty what drugs result in the best performance for each subgroup. Assume that one cycles through a total of N patients, and then select the set of $N_s$ patients who were most successful under their dose of drugs. Estimate, using the technique described above, the parameters $b_s$ for the set of $N_s$ successful patients, and also estimate the set of parameters $b_u$ for the set of $N-N_s$ unsuccessful (or less successful) patients. Then use a similar technique to that described above to ensure that the different between $b_s$ and $b_u$ is statistically significant. In other words, $N_s$ and $N-N_s$ should be large enough such that for some confidence value a that depends on the particular case at hand:

$$|b_{s,p} - b_{u,p}| > t(1-\alpha/2; N_s-\tilde{P})s(b_{s,p}) + t(1-\alpha/2; N-N_s-\tilde{P})s(b_{u,p}); p=1 \ldots \tilde{P} \quad (24)$$

Then, select the top P largest values of $b_s$ to indicate the drugs that should be used on subsequent patients. Note that the method of testing a range of inputs in order to model the response of a system is known in the art as persistent excitation, and there are many techniques for determining more optimally how to collect experimental data to a model a system in an optimal way so that the system can be identified as well as a particular response achieved. One seeks to identify the optimal parameters b and at the same time achieve the greatest positive change in Y for the greatest number of patients. Different methods can be applied than those outlined above without changing the fundamental idea. Of course, one could also test different dosages of drugs as well as testing the drugs in different combinations Another approach to predicting the best possible drug regimen is to predict the outcome for the patient for each of a set of available or recommended drug regimens, and then simply select that regimen which has the best predicted outcome.

It will be clear to one skilled in the art that various other techniques exist for predicting an outcome, or the probability of an outcome, using the relationships in the standardized data model. These different techniques would be stored as different expert statistical models 128. For example, consider one is trying to predict the likelihood of a certain state being reached, such as CD4 count below 200/uL. Rather than use the regression model described above, another approach is to consider the time to progression of the particular outcome. Different time-to-outcome estimates between different treatment methodologies can be compared using techniques that are known in the art such as log-rank tests. In order to evaluate different treatment methodologies from data within the patient data base 108, the time-to-outcome for each group treated in a different manner can be constructed using, for example, the Kaplan-Meier product limit method. It should also be noted that there will often be significant differences between the data in different patient groups which would affect outcome and is not related to the particular variable under consideration, such as for example treatment regimen. This will often occur when data from different clinical studies is aggregated, for example. Methods are known in the art to perform adjusted analyses to compare the time-to-outcome distribution for different groups of patients. For example, the method of Cox's proportional hazards model adjusts for the effect of the covariates that are predictive of progression-to-outcome. For example, in predicting the time to CD4 count below 200/uL, these covariates, in addition to treatment type, will include such factors as age, gender, body mass index, diet, baseline CD4 and viral load counts at time of initial treatment, and treatment adherence. These adjusted comparisons entail score tests that are more powerful because of covariate adjustments. The proportional hazards assumption can be checked by considering the Schoenfeld residuals for significant covariates and interactions. When the proportional hazards assumption is violated, several approaches may be considered. One approach would be to use a stratified proportional hazards model in which the proportional hazards assumption holds within each stratum. Another approach introduces appropriate time-dependent covariates in place of those covariates with hazard functions non-proportional to the baseline hazard. An appropriate Cox model with time-dependent covariates can then be fitted.

Note that many other expert statistical models 128 can be used by the DAME 100 in selecting between different treatment strategies. For example, when the effectiveness of different ART treatments are being compared using outcomes that are continuous in nature, such as the level of CD4 count. A repeated measures Analysis of Variance (ANOVA) could be used to compare mean outcome profiles between different treatment arms. The analysis in this case could use canonical methods such as a Diggle's mixed-effects-model. In this case, treatment type would be a fixed effect (other covariates are possible), while patients will be the random effects. Appropriate transformations such as Box-Cox will be applied to these continuous outcomes to achieve approximately normality. These methods are known to those skilled in the art. Additional canonical methods can be brought to bear on outcomes that are categorical in nature. For example, one might be interested in whether it is more likely for a particular mutation to develop in the HIV virus after the patient is subjected for one year to one ART regiment instead of another. This type of categorical outcome can be analyzed using Fisher's exact test for 2×2 contingency tables using the method of difference-in-proportions to measure dependence. When multiple different ART's are considered, one can use the more general Fisher-Freeman-Halton test with the likelihoods ratio test to determine dependence.

Other Approaches to Statistical Models 128 and Computed Relationships 123 for Predicting Outcome and Validating Subject's Data 108:

Another regression technique, which doesn't change the fundamental idea discussed above, is to take into account the interactions between the independent variables when modeling the response of a dependent variable, so that one no longer treats the system as linear. Instead, the model involves product terms between the dependent variables, and can be displayed in very general form as:

$$Y_n = \beta_0 + \sum_{i=1}^{I-1} \beta_i \prod_{p=0}^{P-1} X_{n,p}^{power_{p,i}} + \varepsilon_n, \quad n = 1 \ldots N \quad (25)$$

where there is a total of I parameters $\beta_i$ to be estimated (or I polynomial terms in the expression), a total of $\tilde{P}$ medicines to be evaluated, and $power_{p,i}$ is the power to which is raised the data referring to the $p^{th}$ medicine, in the $i^{th}$ term with the coefficient $\beta_i$. This is a very general and flexible formulation. Heuristic data fitting and cross-validation are necessary to finding the right set of terms $power_{p,i}$ to model the interaction between the parameters. This can, of course, be applied to all data classes, not just those addressing dosages of medicine. In addition, a wide range of data classes and functions can go into generating the dependent variable, $Y_n$.

Notice that there is nothing in the description provided which restricts the independent variables to be derived from the patient treatment information data class, nor which limits the dependent variable to be derived from the patient symptomatic information data class. One could apply a similar set of techniques to data classes from the patient diagnostic information; including the vast body of genetic data where the set of independent variables refer to whether or not the patient has a particular allele of a particular gene. In this case, the dependent variable could refer to any phenotypic trait, such as height, eye color, propensity for breast cancer, propensity for psoriasis, propensity for heart illness etc. Using the same fundamental techniques described above, the DAME 100 can generate predictions about these phenotypic traits based on the genetic data in the patient diagnostic information data class, as well as based on an assessment of the validity or confidence bounds of these predictions.

In one embodiment, an individual's genetic information is used by the DAME 100 as a tool for Customer Relation Management (CRM), based on the phenotypic predictions that can be made, or expert rules that can be applied to, this genetic information. For example, an individual could ask to have information filtered to suite their individual needs, based on their genetic code. The DAME 100 would forward to this individual via the UI server 102 advertisements, or information about particular items of food, clothing or other items which would match the individual's nutritional needs, physical shape or mental propensities, based on their genetic dispositions. Companies wanting to target marketing effectively could provide a range of marketing material to the system, which could then be forwarded to suitable recipients based on the genetic information and contact information that reside within the data base 110. There are of course a host of other CRM applications, based on either customer pull or seller push to which the system can be applied, using the fundamental concepts disclosed herein.

Additional services, similar to the customer-pull services outlined above, involve individuals interacting with the UI server 102 to ask questions based on genetic information that the individuals provide. The DAME 100 could be used by primary care providers when they prescribe medication tailored for an individual, ranging from medication as general as pain killers, to medication for conditions such as psoriasis, cancer, HIV/AIDS etc. The care provider would submit the subject's genetic and clinical information, in order for the DAME 100 to predict the expected outcome in response to different proposed drugs.

In another usage scenario, two potential parents might provide their genetic information in order for the DAME 100 to predict what would be their probability for producing a child with particular traits such as height, eye-color, probability for psoriasis, probability for breast cancer, particular mental propensities etc. The DAME 100 could make these predictions based on the same concepts disclosed previously. In performing a genetic analysis on a particular phenotypic feature, f, the DAME 100 would perform computation on the genetic data classes known to influence that feature f. For example, if f represents the probability that the individual develops psoriasis, the system would base the genetic analysis on a set of data classes referring to alleles of particular genes, where those alleles affects the likelihood of psoriasis. Let us assume that there are $N_f$ such data classes represented by $X_{n,i}$, i=1 ... $N_f$, where the values of the data classes $X_{n,i}$=1 or 0, depending on whether or not the particular alleles of the relevant genes are present in individual n. Using the general formulation above, and assuming that $Y_N$ represents that feature f for an individual N, $$Y_N = \beta_0 + \sum_{p=1}^{P-1} \beta_p f_p(X_{N,0}, X_{N,1}, \ldots X_{N,N_f-1}) + \varepsilon \quad (26)$$

In many cases of binary data classes, the functions $f_p$ would emulate logical expressions of the dependent variable. For a simple linear model, one could use $P=N_f+1$ parameters as follows:

$$Y_N = \beta_0 + \sum_{p=1}^{P-1} \beta_p X_{N,p} + \varepsilon \quad (27)$$

Subsequent discussion is based on the most general formulation described in (27). Consider the probability of having a particular set of values $(x_0 \ldots x_{p-1})$ for the data classes $X_{N,0} \ldots X_{N,P-1}$, which is denoted $p_{X_{N,0} \ldots X_{N,P-1}}(x_0 \ldots x_{P-1})$. Based on the genetic information describing the alleles of genes on the homologous chromosomes of the parents, it will be straightforward to one skilled in the art to compute the probability $p_{X_{N,0}} \ldots X_{N,P-1}(x_0 \ldots x_{P-1})$ for each possible combination of gene alleles in the child (individual N). For example, consider that data class $X_{N,0}$ is 1 (TRUE) when individual N has allele a of gene g on one or both chromosomes and data class $X_{N,1}$ is 1 (TRUE) when individual N has allele c of gene g on one or more chromosomes. Assume the one parent has alleles a and c of gene g on their homologous chromosomes, and the other parent has alleles d and e of gene g on their homologous chromosomes. Assuming Mendellian independent assortment of genes, one can say $$p_{x_{N0}x_{N1}}(0,0)=0;\ p_{x_{N0}x_{N1}}(1,0)=0.5;\ p_{x_{N0}x_{N1}}(0,1)=0.5;\ p_{x_{N0}x_{N1}}(1,1)=0 \quad (28)$$

One cannot always assume independent assortment since, due to the mechanism of crossover in gamete formation, genes in close proximity on the same chromosome will tend to stay together in the offspring. The proximity of gene loci are measured in centi-Morgans, such that two genetic loci that show a 1% chance of recombination are defined as being 1 cM apart on the genetic map. The rules for computing $p_{x_0 \ldots x_{P-1}}(x_0 \ldots x_{P-1})$ for a progeny, based on the known proximity of the gene loci, the alleles present in the parents, and the mechanisms of meiosis, are well understood and these probabilities can be computed by one skilled in the art of genetics.

Assume that using a regression technique similar to that described above and data records from many individuals, a set of parameters $b_{x_0 \ldots x_{P-1}}$ has been computed, which let us estimate a particular $Y_{N,x_0 \ldots x_{P-1}}$ given a particular data vector $X_{N,x_0 \ldots x_{P-1}}$ according to the matrix formulation $\hat{Y}_{N,x_0 \ldots x_{P-1}} = X_{N,x_0 \ldots x_{P-1}} b_{x_0 \ldots x_{P-1}}$. In this case, $X_{N,x_0 \ldots x_{P-1}}$ is the matrix of values of the independent variables $[x_0 \ldots x_{P-1}]$. Assume that all of the different combination of the independent variables are contained in a set of the combinations: $S_p = \{[x_0 \ldots x_{P-1}]\}$. Based on the genes of the parents, $Y_N$ for the progeny may be estimated by:

$$\hat{Y}_N = \sum_{[x_0 \ldots x_{P-1}] \in S_P} p_{x_0 \ldots x_{P-1}}(x_0 \ldots x_{P-1}) X_{N,x_0 \ldots x_{P-1}} b_{x_0 \ldots x_{P-1}} \quad (29)$$

In addition, for the purpose of understanding the confidence of this estimate, one could compute the estimate of the confidence bounds on $\hat{Y}_N$ using the same technique described above:

$$\hat{Y}_N \pm t\left(1 - \frac{\alpha}{2}, N - P\right) s(\hat{Y}_N - Y_N) \quad (30)$$

For each separate estimate $Y_{N,x_0 \ldots x_{P-1}}$ for a given data set, compute a separate mean-squared error, $MSE_{x_0 \ldots x_{P-1}}$, using the techniques described above. Hence, considering the Equation (35) estimate the variances $(\hat{Y}_N - Y_N)$:

$$s^2(\hat{Y}_N - Y_N) = \sum_{[x_0 \ldots x_{P-1}] \in S_P} p_{x_0 \ldots x_{P-1}}(x_0 \ldots x_{P-1})^2 MSE_{x_0 \ldots x_{P-1}} \quad (31)$$

$$\left(X_{N,x_0 \ldots x_{P-1}}^T (X_{x_0 \ldots x_{P-1}}^T X_{x_0 \ldots x_{P-1}})^{-1} X_{N,x_0 \ldots x_{P-1}} + 1\right)$$

In this way, based on the information collected in the database 110, one can estimate the phenotypic features of progeny, as well as our confidence in those estimates. There are many different techniques for refining these estimates, using the ideas described above and other statistical techniques, without changing the fundamental concept disclosed.

One possible variant on this theme is to analyze the genetic makeup of a male and female gamete to decide whether they should be combined to form a progeny. Since the gamete would typically be destroyed using modern techniques for sequencing its genome, in one embodiment the genetic makeup of the gamete is determined by a process of elimination. This method employs the fact that the genetic information of the parent cell is copied once and distributed among the four gametes produced in meiosis. In this technique, the genetic makeup of the parent cell is determined, as well as of three of the four gametes that result from a meiotic division. This would allow one to determine the genetic makeup of the fourth gamete resulting from the meiotic division, without directly measuring the genetic sequence of that gamete.

Making Inferences with Sparse Data

Consider the scenario, very common in dealing with genetic data, where there are a large number, P, of parameters in comparison to the number of subjects, N. Described here is a method for analyzing sparse data sets which can determine a set of parameters $b = [b_0 b_1 \ldots b_{P-1}]^T$ that can meaningfully map between the independent variables representing some parameters p of patient n, $X_{p,n}$, and some dependent variable or outcome for that patient, $Y_n$. Some types of genetic data that the independent variables can represent are discussed first.

$X_{p,n}$ could be a categorical variable representing whether or not a particular allele $a_p$ is present in the genes of patient n i.e. $X_{p,n}=1$ if allele $a_p$ is present on either of patient n's homologous chromosomes, and $X_{p,n}=0$ if allele $a_p$ is not present in either of patient n's homologous chromosomes. Note that one could also have different categorical variables representing whether the allele is present on only one homologous chromosome, on both homologous chromosomes, or on neither. For example, one could have a variable $X_{dominant,p,n}$ which is 1 if allele $a_p$ is present on either homologous chromosome, and another variable $X_{recessive,p,n}$ which is 1 only if allele $a_p$ is present on both homologous chromosomes. With these types of data, the number of regression parameters P could be many tens of thousands, roughly corresponding to the number of possibly relevant alleles. $X_{p,n}$ could also be a non-categorical continuous variable. For example, $X_{p,n}$ could represent the concentration of a particular type of Ribonucleic Acid (RNA) in the tissue sample of patient n, where that RNA corresponds to the expression of one (or several) alleles, $a_p$, of some gene. In this case as well, P would be on the order of many tens of thousands, corresponding to the number of possibly relevant genetic alleles that could be expressed as RNA in the tissue of a patient. After reading this disclosure, it would be clear to one skilled in the art the range of other categorical and non-categorical variable sets that would give rise to sparse data in the context of genetic analysis.

A versatile formulation of the independent variables, $X_{p,n}$, which is particularly relevant for genetic analysis, is as logical expressions involving other categorical variables. Assume that there are P logical expressions, which may greatly exceed the number of original categorical variables that are combined to form these expressions. For example, consider that there are a set of alleles, numbering A, that can be detected in a genetic sample. Let the variable $\tilde{X}_{a,n}$ be True if allele $a_a$ is present in the sample, and False if allele $a_a$ is not present.

Ignore, for notational simplicity, the question of dominant vs recessive alleles; it will be clear how the method would extend to deal with variables defined for dominant or recessive genetic alleles. Another scenario that the method could address is time-dependent relationships between variables, when one event needs to precede another. To address this, one could take longitudinal data on a particular variables sampled over time, and represent the results in a set of time bins. This would generate multiple independent variables for regression—the number of variables corresponding to the number of time bins—for each longitudinal variable. The number of time bins can be selected using canonical techniques so that the independent variables are not too closely correlated. A continuous variable may be converted into a categorical variable which represents whether or not some threshold was exceeded by the continuous variable.

Consider different combinations of logical expressions that can be created with the set of Boolean variables $\{\tilde{X}_{a,n}, a=0 \ldots A-1\}$. The purpose of the method disclosed is to be able to explore a large range of possible interactions with many variables, even in the context of sparse data. Define the maximum number of independent variables to be used in each term of the logical expression as $V \in [1 \ldots A]$. Note that a logical term is used here to refer to a set of variables, or their complements, that are related to one another by the AND ($\vee$) operator. Assume that multiple terms are combined into a logical expression by the OR ($\vee$) operator. In order to model our dependent variable, Y, create an expression using all of the possible logical combinations of the independent variables. For example, assume $V=A=2$. In other words, one has two different alleles, and one is looking at all logical expressions combining one or both of the corresponding independent variables $\{\tilde{X}_{0,n}, \tilde{X}_{1,n}\}$. Map the Boolean variables into corresponding numerical random variables, $X_{p,n}$, using an Indicator Function, I. For example, $X_{p,n}=I(\tilde{X}_{a,n})=1$ if $\tilde{X}_{a,n}$ is TRUE and 0 otherwise. Then the logical expression with these variables may look like:

$$Y_n = b_0 + b_1 I(\tilde{X}_{0,n}) + b_2 I(\tilde{X}_{1,n}) + b_3 I(\tilde{X}_{0,n} \wedge \tilde{X}_{1,n}) + \qquad (32)$$
$$b_4 I(\tilde{X}_{0,n} \wedge \tilde{X}^c_{1,n}) + b_5 I(\tilde{X}^c_{0,n} \wedge \tilde{X}_{1,n}) + b_6 I(\tilde{X}^c_{0,n} \wedge \tilde{X}^c_{1,n})$$
$$= b_0 + b_1 X_{1,n} + b_2 X_{2,n} + b_3 X_{3,n} + b_4 X_{4,n} + b_5 X_{5,n} + b_6 X_{6,n}$$

where the $^c$ operator denotes the complement of a Boolean variable. Note that one does not include terms involving the complement of only one independent variable. This would be redundant since any expression involving the complement of a single independent variable $\tilde{X}_{a,n}^c$ can be reproduced with $\tilde{X}_{a,n}$ and the same number of regression parameters by redefining the bias term and gradient term. For example, $Y_n=b_0+b_1 I(\tilde{X}_{0,n}^c)$ could be recast in terms of $\tilde{X}_{0,n}$ using $Y_n=(b_0+b_1)-b_1 I(\tilde{X}_{0,n})$. Note that there is also a level of redundancy in including all permutations of terms involving more than one variable, since these terms can be represented in terms of one another. For example, the expression $Y_n=b_0+b_1 L(\tilde{X}_{0,n} \tilde{X}_{1,n})$ could be recast as $Y_n=(b_0+b_1)-b_1 L(\tilde{X}_{0,n} \tilde{X}_{1,n}^c)-b_1 L(\tilde{X}_{0,n}^c \tilde{X}_{1,n})-b_1 L(\tilde{X}_{0,n}^c \tilde{X}_{1,n}^c)$. However one would then be using four non-zero regression parameters instead of two, so the representations are not equivalent in terms of the requisite number of regression parameters needed to weight the expressions, and would not be interchangeable using the method described here. Consequently, one includes the terms corresponding to all permutations of more than one variable.

For example, consider the more general case when $V=2<A$. The expression that captures all resultant combinations of logical terms would then be:

$$Y_n = b_0 + \sum_{i=0}^{A-1} b_{i+1} I(\tilde{X}_{i,n}) + \sum_{i=0}^{A-1} \sum_{\substack{j=0 \ldots A-1, \\ j \neq i}} b_{f(i,j)} I(\tilde{X}_{i,n} \wedge \tilde{X}_{j,n}) + \qquad (33)$$
$$b_{f(i,j)+1} I(\tilde{X}_{i,n} \wedge \tilde{X}^c_{j,n}) + b_{f(i,j)+2} I(\tilde{X}^c_{i,n} \wedge \tilde{X}_{j,n}) + b_{f(i,j)+3} I(\tilde{X}^c_{i,n} \wedge \tilde{X}^c_{j,n})$$
$$= b_0 + \sum_{p=1}^{A} b_p X_p + \sum_{p=A+1}^{P-1} b_p X_p$$

In the second line, one has used some indexing function $f(i,j)$ to denote that the indexes of regression parameters will be some function of i and j without using overly complex notation. Furthermore, in order to simplify notation and without loss of generality, all of the terms in the second line are recast into the set of terms denoted by the last summation of the third line. In general, for any A and V, the number of resulting parameters necessary to combine the logical terms in the expression would be:

$$P = 1 + A + \sum_{j=2}^{V} \binom{A}{j} 2^j \qquad (34)$$

The number of logical terms, and the associated parameters, grow rapidly with an increase in A and V. Techniques are understood in the art for reducing the number of terms in the regression by checking that the independent variables are not too closely correlated. For example, one may start creating independent variables from the logical expressions involving combinations of fewer categorical variables. Each time a new logical expression is added to create a new independent variable, one checks that the correlation coefficient between the new variable and any of the existing variables does not exceed some threshold. This helps to assure a well-conditioned and convergent solution. Many techniques exist in the art to eliminate redundant variables and higher order interaction variables, without changing the essential concept discussed here.

Despite techniques for reducing the variable set, P may still grow to become very large as A and V increase. It is now described how to manage this large number of terms, even though the number of parameters P may considerably exceed the number of outcomes, N. Let the set of outcomes be $\{Y_n, n=0 \ldots N-1\}$. Note that $Y_n$ may be related to a categorical variable; for example $Y=1$ if the patient has a particular disease and $Y=0$ if not. Alternatively, $Y_n$ may be a non-categorical variable such as the probability of the patient developing a particular disease, or the probability of a patient developing resistance to a particular medication within some timeframe. First, the concept is illustrated in general. Different formulations of the dependent variable are discussed below, in particular those related to logistic regression where the outcomes are categorical. In order to use matrix notation, stack the dependent variables for N patients in vector $y=[Y_0 Y_1 \ldots Y_{N-1}]^T$. Represent in matrix notation a linear mapping of the independent variables to the dependent variables according to:

$$y=Xb+\epsilon \qquad (35)$$

Where $$y = \begin{bmatrix} Y_0 \\ \vdots \\ Y_{N-1} \end{bmatrix}, \quad X = \begin{bmatrix} X_{0,0} & \cdots & X_{P-1,0} \\ \vdots & & \vdots \\ X_{0,N-1} & \cdots & X_{P-1,N-1} \end{bmatrix}, \quad (36)$$

$$b = \begin{bmatrix} b_0 \\ \vdots \\ b_{P-1} \end{bmatrix}, \quad \varepsilon = \begin{bmatrix} \varepsilon_0 \\ \vdots \\ \varepsilon_{N-1} \end{bmatrix}$$

where the vectors models disturbances and it is assumed that $X_{0,n}=1$. In the sparse data scenario, it is not possible to compute estimates $\hat{b}$ of the parameters b according to a least squares solution $\hat{b}=(X^T X)^{-1} X^T y$ since the matric $X^T X$ is not invertible. That is to say $X^T X$ is a sparse matrix, and an infinite number of solutions $\hat{b}$ exist that can satisfy the regression equation. The technique described here enables one to create estimates of the parameters in this sparse scenario, where the number of subjects, N, may be much less than P.

Consequently, this method enables us to create complex logical or arithmetic combinations of random variables when the coupling between these random variables is necessary to model the outcome.

In order to restrict the different values of $\hat{b}$ in the sparse scenario, a shrinkage function s is created which is weighted with a complexity parameters $\lambda$. b Is estimated by solving the optimization:

$$\hat{b} = \arg\min_b \|y - Xb\|^2 + \lambda s(b) \quad (37)$$

There are many different forms that s(b) can take, including:

$$s(b) = \sum_j |b|_j \quad (38)$$

$$s(b) = \sum_j b_j^2$$

$$s(b) = \sum_j \ln(|b|_j + \delta)$$

The last formulation is particularly well suited to the case where parameters correspond to a large set of logical expressions, as described above. The theoretical motivation behind this formulation is based on coding theory. In essence, one is trying to find a parameter set $\hat{b}$ that can explain the data while remaining as simple or sparse as possible. Stated differently, one would like to apply "Ockham's Razor" to estimating b. One mathematical approach to describing "simplicity" is to consider the length of a code necessary to capture the information in $\hat{b}$. It can be shown that real numbers can be coded to some precision $\delta$ using a code of length $\log(\lfloor |r|/\delta+1 \rfloor)+O(\log\log(|r|/\delta))$ bits. One may assume that the second term is negligible and focus on the first term. This can be used as a shrinkage function according to:

$$s(b) = \sum_j \log(|b_j|/\delta + 1) = \sum_j \log(|b_j| + \delta) - P\log\delta \quad (39)$$

Since the last term is independent of b, it can be dropped from the shrinkage function, leaving the last function described in (39) above. Hence, one can solve for sparse paramaters according to:

$$\hat{b} = \arg\min_b \|y - Xb\|^2 + \lambda \sum_j \log(|b_j| + \delta) \quad (40)$$

The parameter a can be viewed as the minimum penalty for each coefficient $b_j$ and is often set to 1 in practice although the exact choice will depend on the data, and can be made by one skilled in the art after reading this disclosure. The parameter $\lambda$ represents the conversion factor between the penalty function s(b) and the expression being minimized, in this case the squared residual error $\|y-Xb\|^2$. In particular $\lambda$ represents how many units of residual error one is willing to sacrifice for a reduction of 1 unit of s(b). This optimization equation can be solved using techniques that are known in the art. The general technique involves solving the optimization for pairs of $(\lambda,\delta)$ over some reasonable range, and then using cross-validation with test data and an estimate of the prediction error to select the optimal $(\lambda,\delta)$ pair. For each $(\lambda,\delta)$ pair, the optimization can be solved by techniques that are understood in the art. One such technique involves updating the estimate $\hat{b}$ at each step using a first order approximation of a log function, linearized around the current estimate at update epoch k, $\hat{b}^k$, and then dropping all terms from the minimization expression that are independent of b. The resultant iterative update simplifies to $$\hat{b}^{(k+1)} = \arg\min_b \|y - Xb\|^2 + \lambda \sum_j \frac{|b_j|}{|b_j^{(k)}| + \delta} \quad (41)$$

Since this expression is convex in b, it can be easily solved by a variety of methods to generate the next estimate of b, $\hat{b}^{k+1}$. This process is continued until some convergence criteria is satisfied. A similar method can be applied to logistic regression such as in the case that $Y_n$ is a categorical variable. This will be the case in predictive problems, such as estimating the probability of developing a particular disease or the probability of a viral or bacterial strain developing resistance to a particular medication. In general, logistic regression is useful when the dependent variable is categorical. If a linear probability model is used, $y=Xb+\epsilon$ (35, one can obtain useful results in terms of sign and significance levels of the dependent variables, but one does not obtain good estimates of the probabilities of particular outcomes. This is particularly important for the task of making probabilistic projections based on genetic data. In this regard, the linear probability model suffers from the following shortcomings when used in regression:

1. The error term (or the covariance of the outcome) is dependent on the independent variables. Assume $Y_n=0$ or 1. If $p_{X_n,Y_n=1}$ describes the probability of event $Y_n=1$ for a particular set of independent variables, $X_n$, then the variance of $Y_n$ is $p_{X_n,Y_n=1}(1-p_{X_n,Y_n=1})$ which depends on $X_n$. That violates the classical regression assumption that the variance of $Y_n$ is independent of $X_n$.
2. The error term is not normally distributed since the values of $Y_n$ are either 0 or 1, violating another "classical regression" assumption.
3. The predicted probabilities can be greater than 1 or less than 0, which is problematic for further analysis which involves prediction of probability.

Logistic regression treats the random variable describing the event, $Y_n$, as a dummy variable and creates a different dependent variable for the regression, based on the probability that an event will occur. Denote this random variable, representing the probability that $Y_n=1$, as $P_{Y_n=1}$. With the variable $P_{Y_n=1}$ create the "logit" regression model (ignore the error term here for the sake of simplicity):

$$\log(P_{Y_n=1}/(1-P_{Y_n=1})) = X_n b \tag{42}$$

The expression $\log(P_{Y_n=1}/(1-P_{Y_n=1}))$, or the "log odds ratio", will constrain the prediction of $P_{Y_n=1}$ based on a set of parameters $\hat{b}$ to lie between 0 and 1:

$$\hat{P}_{Y_n=1} = \frac{1}{1 + \exp(-X_n \hat{b})} \tag{43}$$

Rather than use the classic least-squares technique, solve for the parameters $\hat{b}$ using a maximum likelihood method. In other words, looking over all of the events $1 \ldots N$, maximize the likelihood (the aposteriori probability) of all the independent observations. For each observation, the likelihood of that observation is found according to:

$$\hat{P}_{Y_n=1} = \frac{1}{1 + \exp(-X_n \hat{b})} \tag{44}$$

$$\hat{P}_{Y_n=0} = 1 - \hat{P}_{Y_n=1} = \frac{1}{1 + \exp(X_n \hat{b})}$$

For all N observations with outcomes $\{Y_n = y_n, n=0 \ldots N-1\}$ the probability of the estimated collective outcome is computed as $$\hat{P}_{collective} = \prod_{n=0}^{N-1} \hat{P}_{Y_n=y_n} \tag{45}$$

Let us define the set of all indices, n, for which $Y_n=1$ as $S_1$ and the set of indices for which $Y_n=0$ as $S_0$. In order to maximize the collective probability, one can equally minimize the negative of the log of the collective probability. In other words, one can find the maximum likelihood estimate of the parameters by finding $$\hat{b} = \text{argmin}_b - \log(\hat{P}_{collective}) = \tag{46}$$
$$\text{argmin}_b \sum_{n \in S_1} \log(1 + \exp(-X_n b)) + \sum_{n \in S_0} \log(1 + \exp(X_n b))$$

Now, it can be shown that functions of the form $\log(1+\exp(X_n b))$ are convex in the parameter set b and that the sum of convex functions is convex. Hence, one can apply the same approach as described above to the logistic optimization. In other words, one can find $\hat{b}$ that both satisfies the Maximum Likelihood criterion and is sparse, by solving the convex optimization problem:

$$\hat{b} = \text{argmin}_b \sum_{n \in S_1} \log(1 + \exp(-X_n b)) + \tag{47}$$
$$\sum_{n \in S_0} \log(1 + \exp(X_n b)) + \lambda \sum_j \log(|b_j| + \delta)$$

Note that maximum likelihood method and least-squares regression are equivalent in the case of normally distributed residual error. In particular, form a log-odds ratios as explained above, and assume that $$\log(P_{Y_n=y_n}/(1-P_{Y_n=y_n})) = X_n b + \epsilon \tag{48}$$

where $\epsilon$ is distributed normally. Then the exact solution to b using least squares is the same as with the maximum likelihood method. The practical problem is that, even if one might assume normally distributed errors, one might not have enough data to form empirical odds ratios due to sparsity of data. In particular, for any particular combination of the variables X the is empirical odds ration is defined as $$LO(X) = \log\left(\frac{\text{number of } Y_n = 1|X}{\text{number of } Y_n = 0|X}\right) \tag{49}$$

Due to the small number of observations LO(X) is likely to be small or very large and not suitable for the regression. The maximum likelihood solution, given the above, bypasses that problem by deriving the solution from joint likelihood of all the observations at once. The maximum likelihood formulation can be solved by existing tools that are known in the art to rapidly solve convex optimization problems with multiple of variables. This methodology will be relevant to addressing the type of genetic analysis questions that the DAME 100 will encounter. In particular, this method is important for problems of prediction, based on a limited number of patients, and a large quantity of genetic variables with unknown interrelations.

One consideration in assuring good solution to the above problem is choosing the appropriate conversion factor $\lambda$. Assume that the cost function of the least-squares formulation is denoted by R(b), and the cost function of the maximum likelihood formulation is denoted by M(b). In both cases, there is an addititive penalty function s(b). Since the units of the two cost functions R(b) and M(b) are different, the scale of the shrinkage function s(b) must also be appropriately changed. In particular the conversion factor $\lambda$ must be tuned to insure optimality of the solution as well as its coefficient sparsity. $\lambda$ May be tuned based on cross-validation with test data.

Other Approaches to Making Inference based on Genetic Data

Although the discussion has focused on regression analysis methods, many other techniques may also be used in the DAME 100 to either make predictions for, or to validate, subject data based on the data of a related group of subjects. One embodiment is described here in which a decision tree is used by the DAME 100 to predict the response of mutated HIV viruses to particular ART drugs. The data inhaled in the database 110 includes in-vitro phenotypic tests of the HIV-1 viruses from many hundred subjects who have had their viral Reverse Transcriptase (RT) encoding segments sequenced. The independent variables in the statistical model 128 consist of the list of mutations present in the viral RT genetic sequence. The dependent variable in the statistical model 128 consists of phenotypic tests of susceptibility to the Reverse Transcriptase Inhibitor drug AZT. The phenotypic tests are measured in terms of the log of the ratio of the concentration of the drug required to inhibit replication of the mutated HIV-1 by 50%, compared with the concentration of drug required to inhibit replication of the wild-type HIV-1 clone by 50%.

The statistical model makes use of a binary decision tree where each non-terminal node is split based on the values of one of the independent variables—the presence or absence of a particular mutation. At each node, that independent variable is selected that will subdivide the data into two child nodes such that the dependent variable is as homogenous as possible in each of the child nodes. Each terminal node of the tree is assigned a value that most closely matches the values of the independent variables for all subjects that fall in that subgroup 210, or terminal node. In one embodiment, the match is in the least square error sense. After the decision tree has been generated, the tree can be pruned by eliminating those node splits that have least effect on the prediction error. In a preferred embodiment, the pruning level is determined based on cross validation with test data.

Figure 10:
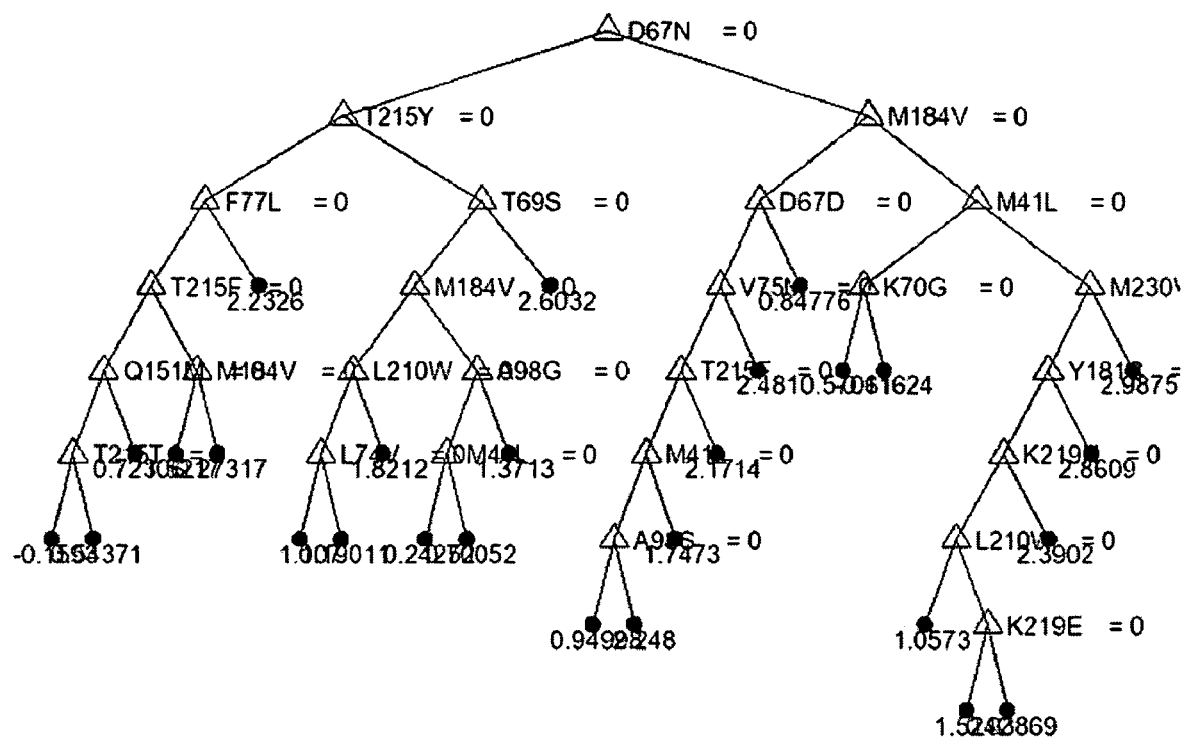
FIG. 10 illustrates a decision tree that was generated using the data from three hundred and four subjects and one hundred and thirty five independent variables to predict the in-vitro phenotypic response of a mutated HIV-1 virus to the AZT Reverse Transcriptase Inhibitor.
Figure 11:
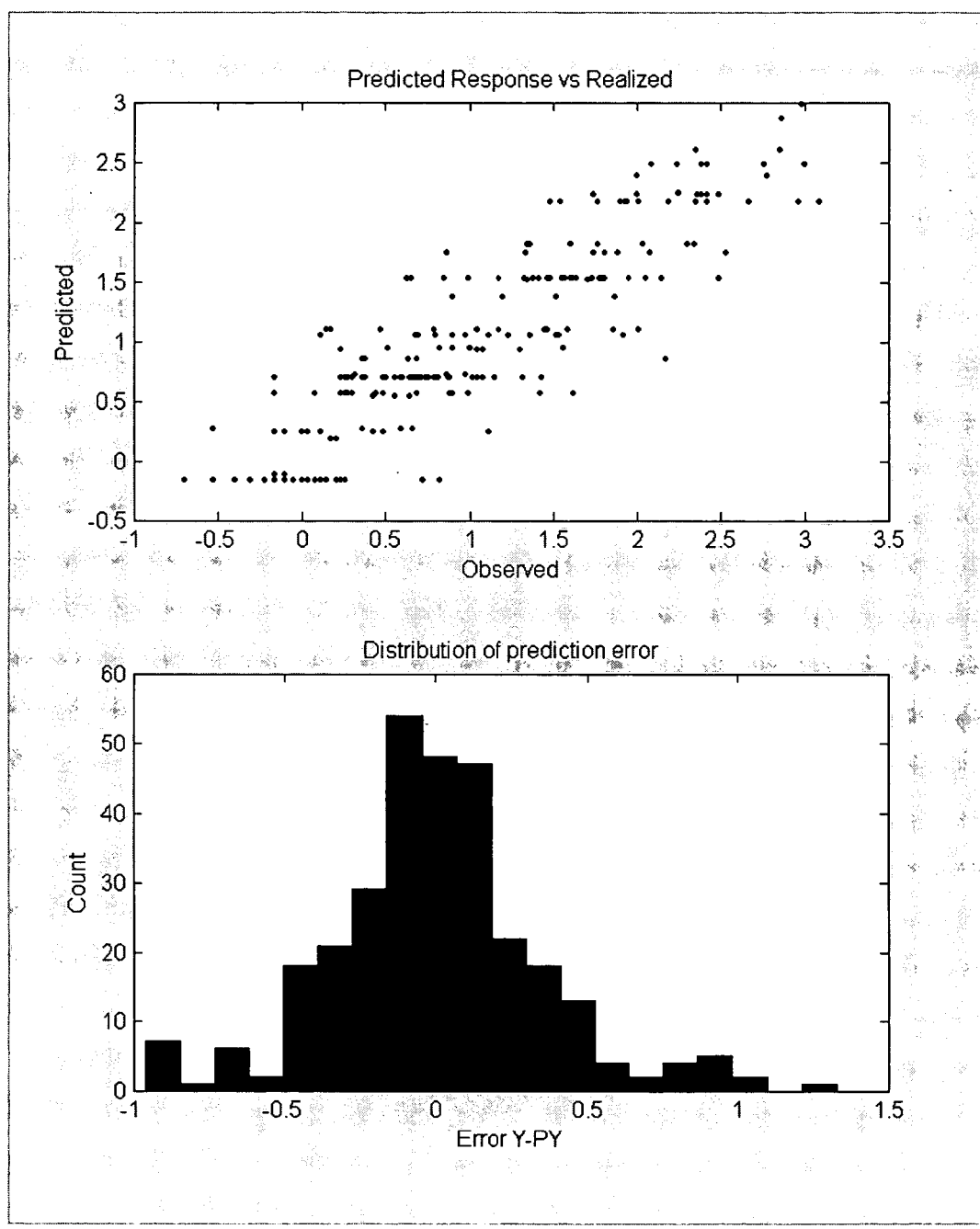
FIG. 11 illustrates the predicted phenotypic response versus the measured phenotype response of the decision tree of FIG. 10, together with a histogram of the prediction error.

FIG. 10 illustrates a decision tree that was generated using the data from three hundred and four subjects and one hundred and thirty five independent variables i.e. 135 mutations from the consensus value in the RT genetic sequence. Note that each mutation is identified with a letter corresponding to the wild-type amino acid, followed by the location on the genetic sequence, followed by the mutated amino acid at that location. The trained and pruned statistical model 128 makes use of 20 variables with 27 terminal nodes. Training the model on 90% of the data, and testing on 10% of the data produced a correlation coefficient between the test data and the phenotype prediction of 0.921. At the time of disclosure, this is well above any the published results that addressing this same issue. FIG. 11 illustrates the predicted response versus the measured phenotype response, together with a histogram of the prediction error.

Enabling a Clinician to Subject multiple Different Statistical Models 128 and Computed Relationships 123 to a Particular Patient's Data 108

FIG. 12 describes the concept of a user interface served by the UI server 102 that will allow a user 401 such as a clinician 106 to subject a patient's data 108 to different statistical models 128 and computed relationships 123 for making predictions of outcome. The different statistical models 128 may come from many different experts, or may come from the statistical models used in electronically published clinical trials, based on recent requirements from the NIH that all results, data, and methods of clinical trials should be published and made accessible electronically. In a preferred embodiment, the raw subject data of the published trials are inhaled into the patient database 110 according to the standardized data model 117; the statistical model used are inhaled into the statistical models 128 of the metadata database 122; the parameters of the model are recomputed and stored in the computed relationships section 124 of the metadata database 122.

In one embodiment, the clinician 106 will access the system on a device with a GUI (Graphical user Interface) served by a GUI server 102 over the Internet 104, and will login using a secure user name and password possibly augmented with biometric authentication. The system will prompt the clinician 106 to enter a patients name or number and the relevant patient record 108 will be retrieved. In one embodiment, the patient's information and the results of a query will be presented to the clinician 106 in 3 sections of the screen detailed below.

Section 1 1200 at the top of the screen, displays:
Patient profile information 112 (i.e. name 1201, number 1202)
System date 1203
Criteria for search 1205, 1206
Two buttons to open screens that display additional genotype information 1207 and phenotype information 1208; and
A Run button 1209

In this embodiment, the additional screens accessible from the phenotype information button 1208 display information such as CD4+ cell count, blood pressure, heart rate etc. and are all date stamped, associated with a validator 109, and in the format of the standardized data model 117. The genotype information button will display such information as known Single Nucleotide Polymorphisms (SNPs) in the genome, and other relevant genetic information associated with key loci in the HIV/AIDS or human genome. The search criteria for the query 105, 106 allows the clinician to perform a "what if scenario" search on existing inhaled statistical models 128 and computed relationships 123. The typical aim, in a preferred embodiment, is to determine what the outcome for the patient would be if subjected to different methods of treatment according to the collection of inhaled models 128. This enables the clinician to see what treatments have been used and analyzed by experts (for example in clinical trials) and determine if they would be suitable for the current patient given the patient's genotypic and phenotype information 108. The search criteria are in a drop down box 1206. In the case of selecting models 128 related to ART for a patient with AIDS, the criteria may include for example: statistical models from the 10 most recent ART trials, statistical models based on the 5 largest ART trials, models from the 3 most recent NIH trials, all available predictive models applied to any patient with HIVAIDS and TB, all available predictive models applied to patients with only HIV/AIDS etc. Once the search criteria have been entered the clinician clicks the run button 1209. This sends the data set of genotype, phenotype information 108 to the DAME 100. The DAME 100 then processes this query using the methods discussed above, and the results are displayed in section 2 and 3.

Section 2 1219 will display the summary results of the query. In one embodiment, it shows a summary of each of the relevant inhaled statistical models 128 (for example, from clinical trials) based on the search criteria supplied. The following information is displayed:
Name of the expert model 128 (or clinical trial) 1220;
Area of focus of model 128 (or trial) (1221);
Trial sample set description 1222 (e.g. patients with TB and HIV/AIDS), highlighting features in common between the current patients data 108 and that of the data used for this statistical model 128;
Date expert statistical model created (or data of clinical trial) 1223;
Current status of expert model or clinical trial (completed, ongoing) 1224;
Number of patients in generating the computed relationship 123 based on the statistical model 128, or the number of subjects in the particular clinical trial 1225;
Organization that created the expert statistical model, or performed the trial 1226;
Notes—free text information about the statistical model or trial 1227;
Predictive outcome using each model for the particular statistical model 1228;

Section 3 1229 will, in a preferred embodiment, display detailed information about one of the statistical models (or trials) highlighted in section 2. There is a drill down functionality from section 2 to section 3. The clinician selects the trial about which to display additional information. The following information is displayed about the statistical model, or trial;
Treatment methodology used 1230;
Name of drugs 1231;
Dosage of each drug 1232;
Time(s) of treatment 1233;
Detailed Trial patient information (i.e. all patients with advanced HIV/AIDS etc.) 1234;
Notes—free text information about the trial 1235;

Additional information request button 1236 (used to request additional information);

Detailed predictive outcome 1237 for patient subjected to the statistical model (or trial methodology) detailed in the section 3.

The predictive outcome is based on the analysis performed by DAME 100 using the relevant statistical model 128, computed relationships 123, and particular patients's data in standardized format 108. The predicted results 1237 would show the probable outcome if the patient had been in the particular trial or following the particular treatment regimen around which the statistical model was based 128. The clinician will then be able to use these predictive outcomes 1237 to administer treatment to the patient or do further investigation. It enables the clinician to make an informative decision about treatment based on clinical trial data. In a preferred embodiment, there is also a predictive outcome on an aggregated level in section 2 1209. This is computed using the techniques discussed above to select the best statistical model, or select the most predictive set of independent variables, and train the model with all the available aggregated data. In one embodiment, all electronically published data models use the same basic format so that the associated data can be easily combined for the purpose of making predicted outcome on an aggregated level. For example, a generic statistical model format for representing the hypothesis of a clinical trial is as 2-by-2 contingency table. The MATLAB code below illustrates a generic template for a training and a mapping function based on a 2-by-2 contingency table, which would allow ease of inhalation and application of the statistical model in the disclosed system. Code is omitted that would be obvious to one skilled in the art. For this illustration, it is assumed that the user of the template is proficient in MATLAB and Structured Query Language (SQL.)

```
%%%%%%%%%%%%%%%%%%%%%%%%%%%%%%%%-
%%%%%%%%%%%%%%%%%%%%%%
% training2by2.m
% This function is an example of a training function for a trial that uses
% a two-by-two contingency table.
%
% Note 1: The function will access all relevant patient data via the data
% structure "patient_struct." This structure contains all the relevant
% information on a patient, formatted according to the standardized
% data model. An API (Application Programming Interface) will specify how
% user can access every element of the standard ontology in MATLAB through
% the patient_struct data structure.
%
% Note 2: The user specifies the inclusion criteria for the trial with set
% of SQL (Structured Query Language) declarative statements operating on
% data classes of the standardized ontology. The user also specifies the
% set of data classes of the standardized ontology that are relevant for
% the training and mapping functions. A standard program will extract all
% relevant patient data using the declarative SQL commands, will package
% that data into the list of "patient_struct"s, and will then call this
% MATLAB function with the list as an input.
function [table2x2, p]=training2by2(patient_list);
% Inputs:
%—patient_list: N×1 matrix of elements of structure "patient_struct."
%
% Outputs:
%—table2x2: a 2×2 matrix of elements of contingency table of the form:
% n11 n12|N1
% n21 n22|N2
%———
% NA NB |N
%—p: 1×1 matrix containing the p-value of the results in table2x2
% counting elements of the contingency table
list_len=length(patient_list);
table2x2=zeros(2,2); % setting 2×2 table with all 0 values
for loop=1:list_len
    patient_str=patient_list(loop); % obtain nth patient struct
    if~meet_incl_Criteria(patient_str) % meet_incl_criteria checks if
        % patient meets inclusion criteria for trial (interface below)
        continue; % if does not meet criteria, go to next element of loop end
    if had_intervention_A(patient_str) % checks if patient
    % meets criteria for intervention A (interface below)
        if had_outcome_1(patient_str) % had_outcome_1 checks if patient
        % meets criteria for outcome 1 (interface below)
            table2x2(1,1)=table2x2(1,1)+1; % updating table count elseif had_outcome 2 (patient_str) % checks if patient % meets creteria for outcome 2. Outcomes 1,2 mutually exclusive.
            table2x2(2,1)=table2x2(2,1)+1; % updating table count end
    elseif had_intervention_B(patient_str) % See above for explanation.
        % function interfaces provided below.
        if had_outcome_1(patient_str)
            table2x2(1,2)=table2x2(1,2)+1;
        elseif had_outcome_2(patient_str)
            table2x2(2,2)=table2x2(2,2)+1;
        end
    end
end
% finding the p-value
p=find_p_2x2_table(table2x2); % this function finds the p-value for 2×2
% contingency table. (defined below)
return;
%%%%%%%%%%%%%%%%%%%%%%%%%%%%%%%%-
%%%%%%%%%%%%%%%%%%%%%%
% mapping.m
% This function is an example of a mapping function for a trial that uses
% a two-by-two contingency table.
function [outcome_prob, prob_bnds_95, prob_bnds_85, prob_bnds_63]=mapping(patient_str, table2x2);
% inputs:
% patient_str—contains all relevant patient data in struct
% patient_struct
% table2x2—2×2 matrix of contingency table, or parameters for mapping
```

```
% outputs:
% outcome_prob—2×1 matrix representing the probability
    of outcome 1
% (first row) and outcome 2 (second row)
% prob_bnds_95—2×2 matrix representing the lower (col-
    umn 1) and upper
% (column 2) probability bounds on outcome_prob(1) (row
    1) and
% outcome_prob(2) (row 2).
% prob_bnds_85—2×2 matrix of the 0.85 probability
    bounds as above
% prob_bnds_63—2×2 matrix of the 0.63 probability
    bounds as above
% setting up variables
outcome_prob=zeros(2,1);
prob_bnds_95=zeros(2,2);
prob_bnds_85=zeros(2,2);
prob_bnds_63=zeros(2,2);
if had_intervention_A(patient_str)
    p11=table2×2(1,1)/(table2×2(1,1)+table2×2(2,1));  %
        finding
    % probability of outome 1 for intervnention A
    outcome_prob=[p11; 1-p11]; % probability of outcome 1
        and 2 for
    % intervention A
    prob_bnds_63=find_binomial_bnds(table2×2(:,1), 0.63);
        % find 63%
    % upper and lower bounds, based on binomial distribution
    prob_bnds_85=find_binomial_bnds(table2×2(:,1), 0.85);
        % find 85%
    % upper and lower bounds, based on binomial distribution
    prob_bnds_95=find_binomial_bnds(table2×2(:,1), 0.95);
        % find 95%
    % upper and lower bounds, based on binomial distribution
elseif had_interventaion_B(patient_str)
    p21=table2×2(1,2)/(table2×2(1,2)+table2×2(2,2));
    % finding probability of outome 1 for intervnention B
    outcome_prob=[p21 1-p21]; % probability of outcome 1
        and 2 for
    % intervention B
    prob_bnds_63=find_binomial_bnds(table2×2(:,2), 0.63);
        % as above,
    % but for intervention B
    prob_bnds_85=find_binomial_bnds(table2×2(:,2), 0.85);
        % as above,
    % but for intervention B
    prob_bnds_95=find_binomialbnds(table2×2(:,2), 0.95);
        % as above,
    % but for intervention B
end
return;
%%%%%%%%%%%%%%%%%%%%%%%%%%%%%%%-
%%%%%%%%%%%%%%%%%%%%%
% function find_p_2×2_table finds the p-value for a 2×2
    contingnecy table.
% Computes this value by finding the log-odds ratio and
    determining the
% probability of the measured or a more extreme log-odds
    ratio under the
% assumption that the null hypothesis holds i.e. that there is
    no
% difference between interveventions.
function p=find_p_2×2_table(table2×2)
% inputs:
% table2×2—2×2 matrix representing a contingency table
% outputs:
% p—1×1 matrix representing the p-value for the table
n11=table2×2(1,1);
n12=table2×2(2,1);
n21=table2×2(1,2);
n22=table2×2(2,2);
N=n11+n12+n21+n22;
log_OR=log((n11/n12)/(n21/n22)); % finding the log odds
    ratio
sigmar_log_OR=sqrt((1/n11)+(1/n12)+(1/n21)+(1/n22)); %
    sample std
deviation
% of log odds ratio
z=log_OR/sigmar_log_OR; % computing test statistic
if z>0
    p=1—cum_dis_fun_z(z, N−1); % cum dis_fun is cumula-
        tive
    % distribution function of test statistic z with N−1 degrees
        of
    % freedom. z is roughly normally distributed for N>=30.
        Use t—
    % distribution for N<30
else
    p=cum_dis_fun(z, N);
end
%%%%%%%%%%%%%%%%%%%%%%%%%%%%%%%-
%%%%%%%%%%%%%%%%%%%%%
% Note 3: Below are the interface for functions
    meet_incl_criteria,
% had_outcome_1, had_outcome_2, had_intervention_A,
    had_intervention_B.
% User will write this MATLAB code to check if the patient
    data meets
% particular criteria, by accessing and analysing the data
    stored in
% patient_struct. All the criteria-matching performed in Mat-
    lab can also
% be performed in SQL, and vice-versa. Larger data sets are
    best filtered
% using SQL for speed. More complex filtering is best per-
    formed in MATLAB
% for flexibility. The user will choose how to distribute the
    analysis
% between SQL and MATLAB.
%%%%%%%%%%%%%%%%%%%%%%%%%%%%%%%-
%%%%%%%%%%%%%%%%%%%%%
% function meet_incl_criteria determines whether a patient
    satisifies all
% inclusion criteria for a trial.
function bool=meet_incl_criteria(patient_str)
% inputs:
% patient_str—a structure of the form patient_struct
% outputs:
% bool—1×1 matrix of value 1 if inclusion criteria met and 0
    if not
<code that analyzes patientstr>
%%%%%%%%%%%%%%%%%%%%%%%%%%%%%%%-
%%%%%%%%%%%%%%%%%%%%%
% function had_intervention_A determines whether a patient
    received the
intervention A
function bool=had_intervention_A(patient_str)
% inputs:
% patient_str—a structure of the form patient_struct
```

```
% outputs:
% bool—1×1 matrix has value 1 if patient had intervention A
     and 0 if not
<code that analyzes patientstr>
%%%%%%%%%%%%%%%%%%%%%%%%%%%%%%%-
    %%%%%%%%%%%%%%%%%%%%%%%
% function had_intervention_B determines whether a patient
    received the intervention A
function bool=had_intervention_B(patient_str)
% inputs:
% patient_str—a structure of the form patient_struct
% outputs:
% bool—1×1 matrix has value 1 if patient had intervention B
     and 0 if not
<code that analyzes patientstr>
%%%%%%%%%%%%%%%%%%%%%%%%%%%%%%%-
    %%%%%%%%%%%%%%%%%%%%%%%
% function had_outcome_1 determines whether a patient
    had outcome 1
function bool=had_outcome_1(patient_str)
% inputs:
% patient_str—a structure of the form patient_struct
% outputs:
% bool—1×1 matrix has value 1 if patient had outcome 1 and
    0 if not
<code that analyzes patientstr>
%%%%%%%%%%%%%%%%%%%%%%%%%%%%%%%-
    %%%%%%%%%%%%%%%%%%%%%%%
% function had_outcome_2 determines whether a patient
    had outcome 2
function bool=had_outcome_2(patient_str)
% inputs:
% patient_str—a structure of the form patient_struct
% outputs:
% bool—1×1 matrix has value 1 if patient had outcome 2 and
    0 if not
<code that analyzes patientstr>
```

Different Implementations of the Invention

The invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

What is claimed is:

1. A method for predicting and outputting a clinical outcome for a first subject, based on a first set of genetic, phenotypic and/or clinical data from the first subject, a second set of genetic, phenotypic and/or clinical data from a group of second subjects for whom a first clinical outcome is known, and a set of statistical models and training methods from published reports of experts, the method comprising:

integrating, on a computer, the second set of data from the group of second subjects into a standardized data model according to a first set of standardized data classes that have unambiguous definition, are related to one another based on computed statistical relationships and/or expert relationships, and encompass at least a portion of all available relevant genetic, phenotypic and clinical data, each standardized data class being represented by a corresponding random variable that describes a corresponding feature;

structuring, on a computer, the first set of data from the first subject according to the first set of standardized data classes, the structured first set of data including first-subject feature values for the features corresponding to the standardized data classes;

automatically selecting, on a computer, from the set of statistical models, a first statistical model for predicting the clinical outcome of the first subject in response to a first intervention based on the first set of standardized data classes and the first and second sets of data by selecting features corresponding to the standardized data classes for the first statistical model to improve a predictive value of the selected features for predicting the clinical outcome, the first statistical model operating to relate the random variables corresponding to the selected features to the clinical outcome;

automatically selecting, on a computer, from the group of second subjects, a patient subgroup with characteristics similar to the first subject by comparing corresponding second-subject feature values with the first-subject feature values for the selected features;

training, on a computer, the first statistical model based on the second set of data from the patient subgroup together with the first clinical outcome of the subgroup of patients;

applying, on a computer, the trained first statistical model to the first set of data of the first subject to predict the clinical outcome for the first subject in response to the first intervention; and outputting the predicted clinical outcome on a fixed medium.

2. A method according to claim 1 wherein the first intervention is automatically selected based on optimizing the expected clinical outcome of the first subject.

3. A method according to claim 1 wherein stored relationships between the standardized data classes, in the form of a first set of expert rules and a second set of statistical models, are used to validate one or more of:

the first set of genetic, phenotypic and/or clinical data for the first subject;

the second set of genetic, phenotypic and/or clinical data for the second subjects;

the prediction of the clinical outcome of the first subject based on the first statistical model; and/or the proposed first intervention based on the prediction of the clinical outcome of the first subject;

and where the second set of statistical models is optionally based on data from the second set of genetic, phenotypic and/or clinical data.

4. A method according to claim 1 wherein the clinical outcome is predicted together with a confidence estimate of the accuracy of that prediction.

5. A method according to claim 1 wherein the first statistical model is automatically selected from multiple relevant statistical models.

6. A method according to claim 1 wherein the set of genetic, phenotypic and/or clinical data for the group of second subjects is derived from multiple different external database systems, and is integrated and formatted according to the set of standardized data classes by means of a cartridge designed to parse the data from each external system.

7. A method according to claim 1 wherein the first statistical model is trained on a data set where the number of elements in the second set is large in comparison to the number of subjects in the second group used to train the model, and the model is trained on the sparse second data set using one or more shrinkage functions.

8. A method according to claim 1 wherein the first statistical model creates independent variables based on logical or arithmetic combinations of the standardized data classes, and the first model is trained using one or more shrinkage functions.

9. A method according to claim 1 wherein the first statistical model creates independent variables based on logical or arithmetic combinations of the first standardized data classes, and the first model is trained using a log shrinkage function designed to minimize the amount of information in a regression parameters set.

10. A method according to claim 1 wherein the first statistical model is trained using the maximum likelihood method of logistic regression, together with a shrinkage function, where the shrinkage function is a log shrinkage function or an absolute magnitude shrinkage function.

11. A method according to claim 1 in which the first statistical model for predicting the clinical outcome of the first subject and the method of training the first statistical model are selected from published statistical models and published methods for training these statistical models,. where those models and methods are published according to a standardized electronic template so that the models and methods can be automatically integrated and applied to the first set of data for the first subject.

12. A method according to claim 1 in which the first set of data includes genetic data for a sperm and egg cell, and the predicted clinical outcome is the probability the progeny resulting from said sperm and egg cell will display a particular phenotypic trait, or multiple phenotypic traits.

13. A method according to claim 1 in which the first set of data includes genetic data of parent organisms, or a parent organism, and the clinical outcome of the first subject is the probability that the progeny of these parent(s) will display a particular phenotypic trait, or multiple phenotypic traits.

14. A method according to claim 1 wherein the first set of data includes genetic data for a set of three gametes resulting from a meiosis division, together with genetic data of the parent organism, from which is determined, by the process of elimination, the genetic information in a fourth preserved gamete; and the clinical outcome of the first subject is the probability that the progeny derived from this preserved gamete will display certain phenotypic features.

15. A method according to claim 1 wherein the first statistical model is continually retrained and refined based on newly integrated and validated data contributing to the data set of second subjects.

16. A method according to claim 1 wherein the first data set comprises genetic mutation data, and the first statistical model comprises a decision tree.

17. A method according to claim 1 wherein the first data comprises genetic mutation data from the HIV viral genome, and the first statistical model comprises a decision tree.

* * * * *

UNITED STATES PATENT AND TRADEMARK OFFICE
CERTIFICATE OF CORRECTION

| | | |
|---|---|---|
| PATENT NO. | : 8,024,128 B2 | Page 1 of 1 |
| APPLICATION NO. | : 11/004274 | |
| DATED | : September 20, 2011 | |
| INVENTOR(S) | : Matthew Rabinowitz et al. | |

It is certified that error appears in the above-identified patent and that said Letters Patent is hereby corrected as shown below:

Col. 46, Ln. 5, after the word "models," Delete "."

Signed and Sealed this
Eighth Day of November, 2011

David J. Kappos
*Director of the United States Patent and Trademark Office*